US006200754B1

(12) United States Patent
Housman et al.

(10) Patent No.: US 6,200,754 B1
(45) Date of Patent: Mar. 13, 2001

(54) INHIBITORS OF ALTERNATIVE ALLELES OF GENES ENCODING PRODUCTS THAT MEDIATE CELL RESPONSE TO ENVIRONMENTAL CHANGES

(75) Inventors: David E. Housman, Newton; Fred D. Ledley, Needham; Vincent P. Stanton, Jr., Belmont, all of MA (US)

(73) Assignee: Variagenics, Inc., Cambridge, MA (US)

( * ) Notice: Subject to any disclaimer, the term of this patent is extended or adjusted under 35 U.S.C. 154(b) by 0 days.

(21) Appl. No.: 09/045,054

(22) Filed: Mar. 19, 1998

(51) Int. Cl.$^7$ .............................. C12Q 1/68; C07H 21/04; C12N 5/00

(52) U.S. Cl. ........................... 435/6; 536/23.1; 536/24.5; 435/375

(58) Field of Search .............................. 435/6, 91.2, 375; 536/23.1, 24.5, 24.3

(56) References Cited

U.S. PATENT DOCUMENTS

| 5,491,064 | 2/1996 | Lichy et al. | 435/6 |
| 5,702,890 | 12/1997 | Housman | 435/6 |

FOREIGN PATENT DOCUMENTS

| 93/23569 | 11/1993 | (WO) . |
| 94/02595 | 2/1994 | (WO) . |
| 94 08473 | 4/1994 | (WO) . |
| 94/11494 | 5/1994 | (WO) . |
| 95/03335 | 2/1995 | (WO) . |
| 97/04087 | 2/1997 | (WO) . |
| 97/32024 | 9/1997 | (WO) . |

OTHER PUBLICATIONS

Abbas, et al., *Cellular and Molecular Immunology*, W.B. Saunders Co. (1991).
Adelman et al., "In Vitro Deletional Mutagenesis for Bacterial Production of the 20,000–Dalton Form of Human Pituitary Growth Hormone," *DNA* 2:183 (1983).
Bolis et al., "A Machine Learning Approach to Computer–Aided Molecular Design," *J. Computer Aided MolecularDesig*, 5:617–628 (1991).
Bussolati, O. Characterization of Apoptotic Phenomena Induced by Treatment with L–Asparaginase in NIH3T3 Cells. *Experimental Cell Research* 220:283–291, 1995.
Cooper, et al., "An Estimate of Unique DNA Sequence Heterozygosity in the Human Genome," *Human Genetics*, 69:201–205 (1985).
Creighton, T.E., Proteins: Structure and Molecular Properties, W.H. Freeman & Co., San Francisco, pp. 79–86 (1983).
Crooke & Bennett, "Progress in Antisense Oligonucleotide Therapeutics," *Annual Rev. Pharm. and Toxicol.* 36:107–129 (1996).

Van Diemen, P.C., X–ray–sensitivity of lymphocytes of aplastic– and Diamond–Blackfanemia patients as detected by conventional cytogentic and chromosome painting techniques. *Mutation Research*, 373:225–235 (1997).
Dixon, "Computer–Aided Drug Design: Getting the Best Results," *Trends in Biotechnology*, 10:357–363 (1992).
Edara, et al., "Resistance of the human 06–alkyguanine–DNA alkytransferase containing arginine at codon 160 to inactivation by 06–bencylguanine," *Cancer Research* 56:5571–5575, 1996.
Fingl et al., in *The Pharmacological Basis of Therapeutics*, 1975, Ch. 1 p. 1.
Hibert et al., "Receptor 3D–Models and Drug Design," *Therapie*(Paris) 46:445–451 (1991).
Holzmayer et al., "Isolation of dominant negative mutants and inhibitory antisense RNA sequences by expression selection of random DNA fragments," *Nucleic Acids Research* 20:711–717 (1992).
Imai et al., A polymorphism at codon 160 of human 06–methylguanine–DNA methyltransferase gene in young patients with adult type cancer and functional assay. *Carcinogenesis* [London] 16:2441–2445, 1995.
Kharbanda, S., et al., "Activation of the c–Abl Tyrosine Kinase in the Stress Response to DNA–Damaging Agents," *Nature*376:785–788, 1995.
Klopman, "Multicase 1: A Hierarchical Computer Automated Structure Evaluation Program," *Quantive Structure–Activity Relationships* 11:176–184 (1992).
Kuntz, "Structure–Based Strategies for Drug Design and Discovery," *Science* 257:1078–1082 (1992).
Lasko, Cavenee, and Nordenskjold, "Loss of Constitutional Heterozygosity in Human Cancer," *Ann. Rev. Genetics*, 25:281–314 (1991).
Lawrence and Davis, "CLIX: A Search Algorithm for Finding Novel Ligands Capable of Binding Proteins of Known Three–Dimensional Structure," *Proteins Structure Functional Genetics* 12:31–41 (1992).
McShan et al., "Inhibition of Transcription of HIV–1 in Infected Human Cells by Oligodeoxynucleotides Designed to Form DNA Triple Helices," *J. Biol. Chem.* 267–5712–5712 (1992).
Miller and Ts'O, "A New Approach to Chemotherapy Based on Molecular Biology and Nucleic Acid Chemistry: Matagen (Masking Tape for Gene Expression)," *Anti–Cancer Drug Des.* 2:11–128 (1987).
Milligan et al., "Current Concepts in Antisense Drug Design," *J. Med. Chem.* 36:1923–1937 (1993).
Mitelman, F., *Catalog of chromosome Aberrations in Cancer* New York: Liss (1988).

(List continued on next page.)

Primary Examiner—Robert A. Schwartzman
Assistant Examiner—Janet L. Epps

(57) ABSTRACT

Disclosed are methods for the treatment of proliferative disorders using compounds and/or environmental conditions which result in a difference in sensitivity of targeted and non-targeted cells. Certain of the methods involve the identification and use of allele-specific inhibitors of conditionally essential genes.

13 Claims, 3 Drawing Sheets

OTHER PUBLICATIONS

Moschel et al & Pegg, "Structural Features of Substituted Purine Derivatives Compatible with Depletion of Human 06–alkylguanine–DNA Alkyltransferase," *J.Med. Chem.*, 35:4486–4491, (1992).

Nicolas, N., et al., "Lack of Detectable Defect in DNA Double–Strand Break Repair and DNA–dependent Protein Kinase Activity in Radiosensitive Human Severe Combined Immunodeficiency Fibroblasts," *Eur. J. Immunol.* 36:1118–1122 (1996).

Nobori et al., "Genomic cloning of methylthioadensoine phosphorylase: A purine metabolic enzyme deficient in multiple different cancers," *Proc. Natl. Acad. Sci. USA* 93:6203–6208 (1996).

Norman, et al., "A Structure–Based Library Approach to Kinase Inhibitors," *J. Am. Chem. Soc.* 118:7430–7431 (1996).

Ohnuma, et al., "Biochemical and Pharmacological Studies with Asparaginase in Man," *Cancer Research* 30: 2297–2305 (1970).

Pastor et al., "The Edisdar Programs Rational Drug Series Design," *Quantive Structure–Activity Relationships*, 10:350–358 (1991).

Piper et al., "Studies Aided by Molecular Graphics of Effects of Structural Modifications on the Binding of Antifolate Inhibitors to Human Dihydrofolate Reductase," *Proc. Am. Assoc. Cancer Res. Annual Meeting* 33:412 (1992).

Poirson–Bichat, F., et al., "Growth of methionine–dependent human prostate cancer(PC–3) is inhibited by ethionine combined with methioine starvation," *Br. J. Cancer* 75:1605–1612 (1997).

*Remington's Pharmaceutical Sciences*, 18$^{th}$ ed., Mack Publishing Co., Easton, PA (1990).

Reynolds et al., "Triple–Strand–Forming Methylphosphonate Oligodeoxynucleotides Targeted to mRNA Efficiently Block Protein Synthesis," *Proc. Nat. Acad. Sci. USA*, 91:12433–12437 (1994).

Savino, et al., Mutations in the Fanconi Anemia Group A Gene (FAA) in Italian Patients. *American Journal of Human Genetics* 61:1246–1253, (1997).

Schwab et al., Antisense Oligonucleotides Adsorbed to Polyalkylcyanoacrylate Nanoparticles Specifically Inhibit Mutated Ha–ras–mediated Cell Proliferation and Tumorigenicity in Nude Mice *Proc. Natl. Acad. Sci. USA*, 91:10460–10464 (1994).

Scott et al., "Searching for Peptide Ligands with an Epitope Library," *Science* 249:386–390 (1990).

Scriver, et al., *The Metabolic and Molecular Bases of Inherited Disease*, 7$^{th}$ edition, McGraw Hill, New York, pp. 3111–3128 and 3129–3149 (1995).

Seizinger et al., "Report of the committee on chromosomes and gene loss in neoplasia," *Cytogenet. Cell Genetics*, 58:1080–1096 (1991).

Silverman, *The Organic Chemistry of Drug Design and Drug Action*, Academic Press (1992).

Stathdee, C.A., et al., Evidence for at least four Fanconi anaemia genes including FACC on chromosome 9. *Nature Genetics* 1:196–198 (1992).

Tan et al., "Anticancer Efficacy of Methioninase in Vivo," *Anticancer Research* 16:3931–3936 (1996).

Terashima et al., "Inhibition of human 06–alkylguanine–DNA alkytransferase and potentiation of the cytotoxicity by 4(6)–(Bencyloxy)2,6(4)–diamino–5–(nitro or nitroso)pyrimidine derivatives and analogues," *J. Med. Chem.* 41:503–508 (1998).

Thacker, J. et al. "The Genetic basis of cellular recovery from radiation damage: Response of the radiosensitive irs lines to low–dose–rate irradiation," *Radiation Research* 144:294–300 (1995).

Thompson, L.H., et al., "Nomenclature of human genes involved in ionizing radiation sensitivity," *Mutation Research* 337:131–134, (1995).

Tisdale, M.J., "Methionine Synthesis from 5'–medthylthioadenosine by Tumor Cells," *Biochemical Pharmacology* 32:2915–2920. (1983).

Trojan, J., et al., "Treatment and prevention of rat glioblastoma by immunogenic C6 cells expressing antisense insulin-–like growth factor I RNA," *Science*, 259:94–97 (1993).

Tsuzuki et al., "Targeted disruption of the DNA repair methyltransferase gene renders mice hypersensitive to alkylation agent," *Carcinogenesis*, 17:1215–1220,(1996).

Yokota, et al., "cDNA Cloning and Chromosome Mapping of Human Dihydropyrimidine Dehydrogenase, an Enzyme Associated with 5–fluorouracil Toxicity and Congenital Thymine Uraciluria," *Journal of Biological Chemistry.* 269:23192–23196, (1994).

Zdienicka, M,Z., "Mammalian mutants defective in the response to ionicing radiation–induced DNA damage," *Mutation Research* 336:203–213,(1995).

Figure 1

Target Variances by Field Table for Conditionally Essential Genes

Conditionally Essential Biosynthetic Enzymes
Validation: Conditionally Essential

| ID | Name | Variances Identified | Chromosome | Genbank Sequence |
|---|---|---|---|---|
| 1536 | 5-methyltetrahydrofolate-homocysteine methyltransferase | 3 | | U75743 |
| 1539 | Glutamate-ammonia ligase (glutamine synthase) | 5 | 1q31 | X59834 |

Proteins that Repair Radiation Induced DNA Damage
Validation: Conditionally Essential

| ID | Name | Variances Identified | Chromosome | Genbank Sequence |
|---|---|---|---|---|
| 1541 | Fanconi anemia complementation group C | 1 | 9q22.3 | X66894 |

Proteins of DNA Repair
Validation: Conditionally Essential

| ID | Name | Variances Identified | Chromosome | Genbank Sequence |
|---|---|---|---|---|
| 1528 | DNA excision repair protein ERCC5 | 4 | 13q33 | D16305 |
| 1530 | HHR23A protein | 3 | 9 | D21235 |
| 1532 | DNA EXCISION REPAIR PROTEIN ERCC-1 | 2 | 19q13.2-q13.3 | M13194 |
| 1533 | DNA repair helicase ERCC3 | 1 | 2q21 | M31899 |
| 1537 | URACIL-DNA GLYCOSYLASE 1 PRECURSOR | 2 | 8 | X15653 |
| 1526 | Damage-specific DNA binding protein 1 (127 kD) | 2 | 11, 15 | AJ002955 |

Proteins that repair chemically induced DNA damage
Validation: Conditionally Essential

| ID | Name | Variances | Chromosome | Genbank |
|---|---|---|---|---|
| 1534 | O-6-methylguanine-DNA methyltransferase | 4 | 10q26 | M60761 |

Figure 2-1

| Target ID | Loc'n | Sequence around polymorphism | # Varia 1 (Lib) | # Varia 2 (Lib) | Protein Change |
|---|---|---|---|---|---|
| 1521.6 | 851 | AGACTCTGAG[G/C]CCTGGTGTGA | 7 (6) | 2 (2) | Arg -> Ser |
| .10 | 976 | TTGGGAATGG[A/G]TATCAGAAGA | 15 (8) | 4 (1) | 3' UT |
| .15 | 1165 | TCACCTATAC[A/G]TTATTTAAAT | 20 (8) | 4 (1) | 3' UT |
| .17 | 1236 | GAAAACTGTG[C/A]AATTGTGTGC | 7 (4) | 3 (1) | 3' UT |
| 1523.7 | 417 | CACCACGGTG[C/T]TGGAATTGTT | 9 (8) | 3 (3) | Silent |
| 1524.13 | 2996 | AAAATGACAT[T/G]AGTTTGAAAA | 3 (2) | 3 (2) | 3' UT |
| .22 | 3384 | AACAGCTTTT[A/T]GGCCAAGCTG | 20 (9) | 4 (4) | 3' UT |
| .23 | 3385 | ACAGCTTTTA[G/A]GCCAAGCTGG | 16 (7) | 6 (5) | 3' UT |
| .25 | 3397 | CCAAGCTGGC[C/T]TGACGGTATG | 25 (11) | 4 (3) | 3' UT |
| .26 | 3398 | CAAGCTGGCC[T/G]GACGGTATGG | 25 (11) | 3 (2) | 3' UT |
| 1526.6 | 2476 | TGGAGGTGCA[T/C]AACCTACTTA | 2 (1) | 2 (1) | Silent |
| .7 | 2715 | GTGAAAGGGG[A/C]CGTGTACTCT | 2 (2) | 3 (1) | Asp -> Ala |
| 1528.6 | 770 | CCAAAAGGAA[G/A]TGAATCAGCA | 2 (2) | 2 (2) | Val -> Met |
| .10 | 2396 | GCAGTGCGCA[A/T]TCCTGGACCT | 1 (1) | 4 (4) | Val -> Phe |
| .26 | 3317 | TTCAAGTGAA[G/C]ATGCTGAAAG | 12 (8) | 7 (6) | Asp -> His |
| .32 | 3598 | TATAATTAGT[T/C]ATGACAGCCA | 19 (16) | 2 (1) | 3' UT |
| 1530.8 | 427 | ATCCGCCCCC[A/G]CGACGTCCCC | 4 (3) | 2 (1) | Thr -> Ala |
| .13 | 894 | TGCTGAACGA[G/A]CCCCCTGGGG | 8 (5) | 2 (1) | Ser -> Glu |
| .30 | 1579 | AGTCCTGAAA[G/A]GCCCAAGGCC | 4 (3) | 7 (6) | 3' UT |
| 1532.6 | 496 | TCGTGCGCAA[C/T]GTGCCCCTGGG | 4 (2) | 6 (3) | Silent |
| .10 | 963 | CTGGCCTTAT[G/T]CCCAGGCCTG | 6 (4) | 2 (2) | Cys -> Phe |
| 1533.12 | 2092 | GTATCCCCAGG[A/G]CACACAGGAA | 3 (3) | 2 (2) | Asp -> Ala |
| 1534.4 | 264 | CCGTGCCGGC[A/T]CTTCACCATC | 2 (1) | 5 (4) | Silent |

Figure 2-2

| Target ID | Loc'n | Sequence around polymorphism | # Varia 1 (Lib) | # Varia 2 (Lib) | Protein Change |
|---|---|---|---|---|---|
| 1536.22 | 6641 | TTAGATATAT[A/G]TATTCATTCT | 3 ( 3) | 4 ( 3) | 3' UT |
| .24 | 6779 | ATTTTTATTG[G/A]GCCCAAAAAC | 2 ( 2) | 11 ( 8) | 3' UT |
| .28 | 7097 | AGTGGAATGT[T/A]TAAAAAAAAA | 4 ( 3) | 4 ( 3) | 3' UT |
| 1537.5 | 871 | AGGGCAGTGC[C/A]ATTGATAGGA | 7 ( 6) | 3 ( 3) | Silent |
| .10 | 1466 | GCAGGCATGC[C/A]AGTCTCTGCC | 7 ( 7) | 3 ( 3) | 3' UT |
| 1538.21 | 938 | CCTCCACCTT[T/C]GACGCTGGGG | 14 ( 7) | 3 ( 2) | Silent |
| 1539.1 | 67 | TCGCGGCCTA[G/C]CTTTACCCGC | 3 ( 3) | 2 ( 1) | 5' UT |
| .3 | 304 | TCGATGGCTC[T/C]AGTACTTTAC | 4 ( 4) | 4 ( 3) | Silent |
| .9 | 1075 | GTAGCGCCAG[A/C]CTACGCATTC | 2 ( 2) | 3 ( 2) | Arg -> Ser |
| .16 | 2048 | CAAGGAAGTG[G/A]TTCTTAGATG | 8 ( 7) | 4 ( 2) | 3' UT |
| .21 | 2718 | GCCTAACATAA[A/G]AAAAAAAAAA | 8 ( 8) | 3 ( 3) | 3' UT |
| 1541.1 | 4123 | TGGCGAGGGG[G/C]CTTGACGGCG | 2 ( 1) | 2 ( 2) | 3' UT |
| 1543.4 | 319 | GCACCGGAAG[G/A]AGGCGCTGAC | 6 ( 5) | 2 ( 2) | Ser -> Lys |
| 1544.3 | 534 | TTGAGCCCAA[C/G]TGCTTGGACG | 2 ( 2) | 7 ( 4) | Asn -> Lys |
| .4 | 543 | ACTGCTTGGA[C/T]GCCTTCCCAA | 4 ( 4) | 7 ( 4) | Silent |
| .8 | 643 | ACCTGTGTTC[T/A]CAAAGATGGC | 12 ( 8) | 3 ( 3) | Ser -> Thr |
| .12 | 728 | GCTGCCCAGG[C/G]TGTGCAGCGC | 12 (11) | 4 ( 1) | 3' UT |
| .21 | 902 | AACATCCCCT[C/T]CCATCATTAC | 5 ( 4) | 4 ( 2) | 3' UT |
| .22 | 986 | CTGCCTGGCC[C/T]CTCGCCTGTG | 5 ( 4) | 2 ( 2) | 3' UT |
| 1545.4 | 1470 | CGGTGAGACC[G/A]TTGCCCGCTG | 2 ( 1) | 2 ( 2) | Val -> Ile |
| 1546.1 | 172 | CTCTGAAGAC[A/T]TGGAGATACT | 3 ( 1) | 3 ( 3) | Met -> Leu |

SEQUENCE LISTING

<160> NUMBER OF SEQ ID NOS: 44

<210> SEQ ID NO 1
<211> LENGTH: 21
<212> TYPE: DNA
<213> ORGANISM: Homo sapiens
<220> FEATURE:
<223> OTHER INFORMATION: The letter "s" stands for c or g.

<400> SEQUENCE: 1
agactctgag scctggtgtg a                                              21

<210> SEQ ID NO 2
<211> LENGTH: 21
<212> TYPE: DNA
<213> ORGANISM: Homo sapiens
<220> FEATURE:
<223> OTHER INFORMATION: The letter "r" stands for a or g.

<400> SEQUENCE: 2
ttgggaatgg rtatcagaag a                                              21

<210> SEQ ID NO 3
<211> LENGTH: 21
<212> TYPE: DNA
<213> ORGANISM: Homo sapiens
<220> FEATURE:
<223> OTHER INFORMATION: The letter "r" stands for a or g.

<400> SEQUENCE: 3
tcacctatac rttatttaaa t                                              21

<210> SEQ ID NO 4
<211> LENGTH: 21
<212> TYPE: DNA
<213> ORGANISM: Homo sapiens
<220> FEATURE:
<223> OTHER INFORMATION: The letter "m" stands for c or a.

<400> SEQUENCE: 4
gaaaactgtg maattgtgtg c                                              21

<210> SEQ ID NO 5
<211> LENGTH: 21
<212> TYPE: DNA
<213> ORGANISM: Homo sapiens
<220> FEATURE:
<223> OTHER INFORMATION: The letter "y" stands for c or t.

<400> SEQUENCE: 5
caccacggtg ytggaattgt t                                              21

<210> SEQ ID NO 6
<211> LENGTH: 21
<212> TYPE: DNA
<213> ORGANISM: Homo sapiens
<220> FEATURE:
<223> OTHER INFORMATION: The letter "k" stands for t or g.

<400> SEQUENCE: 6
aaaatgacat kagtttgaaa a                                              21

<210> SEQ ID NO 7
<211> LENGTH: 21

```
<212> TYPE: DNA
<213> ORGANISM: Homo sapiens
<220> FEATURE:
<223> OTHER INFORMATION: The letter "w" stands for a or t.

<400> SEQUENCE: 7
aacagctttt wggccaagct g                                              21

<210> SEQ ID NO 8
<211> LENGTH: 21
<212> TYPE: DNA
<213> ORGANISM: Homo sapiens
<220> FEATURE:
<223> OTHER INFORMATION: The letter "r" stands for g or a.

<400> SEQUENCE: 8 acagcttttta rgccaagctg g                                             21

<210> SEQ ID NO 9
<211> LENGTH: 21
<212> TYPE: DNA
<213> ORGANISM: Homo sapiens
<220> FEATURE:
<223> OTHER INFORMATION: The letter "y" stands for c or t.

<400> SEQUENCE: 9
ccaagctggc ytgacggtat g                                              21

<210> SEQ ID NO 10
<211> LENGTH: 21
<212> TYPE: DNA
<213> ORGANISM: Homo sapiens
<220> FEATURE:
<223> OTHER INFORMATION: The letter "k" stands for t or g.

<400> SEQUENCE: 10
caagctggcc kgacggtatg g                                              21

<210> SEQ ID NO 11
<211> LENGTH: 21
<212> TYPE: DNA
<213> ORGANISM: Homo sapiens
<220> FEATURE:
<223> OTHER INFORMATION: Damage-specific DNA binding protein 1 (127 kD)
<220> FEATURE:
<223> OTHER INFORMATION: The letter "y" stands for t or c.

<400> SEQUENCE: 11
tggaggtgca yaacctactt a                                              21

<210> SEQ ID NO 12
<211> LENGTH: 21
<212> TYPE: DNA
<213> ORGANISM: Homo sapiens
<220> FEATURE:
<223> OTHER INFORMATION: Damage-specific DNA binding protein 1 (127 kD)
<220> FEATURE:
<223> OTHER INFORMATION: The letter "m" stands for a or c.

<400> SEQUENCE: 12
gtgaaagggg mcgtgtactc t                                              21

<210> SEQ ID NO 13
<211> LENGTH: 21
<212> TYPE: DNA
<213> ORGANISM: Homo sapiens
<220> FEATURE:
```

```
<223> OTHER INFORMATION: DNA excision repair protein ERCC5
<220> FEATURE:
<223> OTHER INFORMATION: The letter "r" stands for g or a.

<400> SEQUENCE: 13
ccaaaaggaa rtgaatcagc a                                              21

<210> SEQ ID NO 14
<211> LENGTH: 21
<212> TYPE: DNA
<213> ORGANISM: Homo sapiens
<220> FEATURE:
<223> OTHER INFORMATION: DNA excision repair protein ERCC5
<220> FEATURE:
<223> OTHER INFORMATION: The letter "w" stands for a or t.

<400> SEQUENCE: 14
gcagtgcgca wtcctggacc t                                              21

<210> SEQ ID NO 15
<211> LENGTH: 21
<212> TYPE: DNA
<213> ORGANISM: Homo sapiens
<220> FEATURE:
<223> OTHER INFORMATION: DNA excision repair protein ERCC5
<220> FEATURE:
<223> OTHER INFORMATION: The letter "s" stands for g or c.

<400> SEQUENCE: 15
ttcaagtgaa satgctgaaa g                                              21

<210> SEQ ID NO 16
<211> LENGTH: 21
<212> TYPE: DNA
<213> ORGANISM: Homo sapiens
<220> FEATURE:
<223> OTHER INFORMATION: DNA excision repair protein ERCC5
<220> FEATURE:
<223> OTHER INFORMATION: The letter "y" stands for t or c.

<400> SEQUENCE: 16
tataattagt yatgacagcc a                                              21

<210> SEQ ID NO 17
<211> LENGTH: 21
<212> TYPE: DNA
<213> ORGANISM: Homo sapiens
<220> FEATURE:
<223> OTHER INFORMATION: HHR23A protein
<220> FEATURE:
<223> OTHER INFORMATION: The letter "r" stands for a or g.

<400> SEQUENCE: 17
atccgccccc rcgacgtccc c                                              21

<210> SEQ ID NO 18
<211> LENGTH: 21
<212> TYPE: DNA
<213> ORGANISM: Homo sapiens
<220> FEATURE:
<223> OTHER INFORMATION: HHR23A protein
<220> FEATURE:
<223> OTHER INFORMATION: The letter "r" stands for g or a.

<400> SEQUENCE: 18
tgctgaacga rccccctggg g                                              21
```

```
<210> SEQ ID NO 19
<211> LENGTH: 21
<212> TYPE: DNA
<213> ORGANISM: Homo sapiens
<220> FEATURE:
<223> OTHER INFORMATION: HHR23A protein
<220> FEATURE:
<223> OTHER INFORMATION: The letter "r" stands for g or a.

<400> SEQUENCE: 19
agtcctgaaa rgcccaaggc c                                              21

<210> SEQ ID NO 20
<211> LENGTH: 21
<212> TYPE: DNA
<213> ORGANISM: Homo sapiens
<220> FEATURE:
<223> OTHER INFORMATION: DNA Excision Repair Protein ERCC-1
<220> FEATURE:
<223> OTHER INFORMATION: The letter "y" stands for c or t.

<400> SEQUENCE: 20
tcgtgcgcaa ygtgccctgg g                                              21

<210> SEQ ID NO 21
<211> LENGTH: 21
<212> TYPE: DNA
<213> ORGANISM: Homo sapiens
<220> FEATURE:
<223> OTHER INFORMATION: DNA Excision Repair Protein ERCC-1
<220> FEATURE:
<223> OTHER INFORMATION: The letter "k" stands for g or t.

<400> SEQUENCE: 21
ctggccttat kcccaggcct g                                              21

<210> SEQ ID NO 22
<211> LENGTH: 21
<212> TYPE: DNA
<213> ORGANISM: Homo sapiens
<220> FEATURE:
<223> OTHER INFORMATION: DNA Repair Helicase ERCC3
<220> FEATURE:
<223> OTHER INFORMATION: The letter "r" stands for a or g.

<400> SEQUENCE: 22
gtatcccagg rcacacagga a                                              21

<210> SEQ ID NO 23
<211> LENGTH: 21
<212> TYPE: DNA
<213> ORGANISM: Homo sapiens
<220> FEATURE:
<223> OTHER INFORMATION: O-6-methylguanine-DNA methyltransferase
<220> FEATURE:
<223> OTHER INFORMATION: The letter "w" stands for a or t.

<400> SEQUENCE: 23
ccgtgccggc wcttcaccat c                                              21

<210> SEQ ID NO 24
<211> LENGTH: 21
<212> TYPE: DNA
<213> ORGANISM: Homo sapiens
<220> FEATURE:
<223> OTHER INFORMATION: 5-methyltetrhydrofolate-homocysteine
      methyltransferase
<220> FEATURE:
<223> OTHER INFORMATION: The letter "r" stands for a or g.
```

<400> SEQUENCE: 24
ttagatatat rtattcattc t                                              21

<210> SEQ ID NO 25
<211> LENGTH: 21
<212> TYPE: DNA
<213> ORGANISM: Homo sapiens
<220> FEATURE:
<223> OTHER INFORMATION: 5-methyltetrhydrofolate-homocysteine
      methyltransferase
<220> FEATURE:
<223> OTHER INFORMATION: The letter "r" stands for g or a.

<400> SEQUENCE: 25
atttttattg rgcccaaaaa c                                              21

<210> SEQ ID NO 26
<211> LENGTH: 21
<212> TYPE: DNA
<213> ORGANISM: Homo sapiens
<220> FEATURE:
<223> OTHER INFORMATION: 5-methyltetrhydrofolate-homocysteine
      methyltransferase
<220> FEATURE:
<223> OTHER INFORMATION: The letter "w" stands for t or a.

<400> SEQUENCE: 26
agtggaatgt wtaaaaaaaa a                                              21

<210> SEQ ID NO 27
<211> LENGTH: 21
<212> TYPE: DNA
<213> ORGANISM: Homo sapiens
<220> FEATURE:
<223> OTHER INFORMATION: Uracil-DNA Glycosylase 1 Precursor
<220> FEATURE:
<223> OTHER INFORMATION: The letter "m" stands for c or a.

<400> SEQUENCE: 27
agggcagtgc mattgatagg a                                              21

<210> SEQ ID NO 28
<211> LENGTH: 21
<212> TYPE: DNA
<213> ORGANISM: Homo sapiens
<220> FEATURE:
<223> OTHER INFORMATION: Uracil-DNA Glycosylase 1 Precursor
<220> FEATURE:
<223> OTHER INFORMATION: The letter "m" stands for c or a.

<400> SEQUENCE: 28
gcaggcatgc magtctctgc c                                              21

<210> SEQ ID NO 29
<211> LENGTH: 21
<212> TYPE: DNA
<213> ORGANISM: Homo sapiens
<220> FEATURE:
<223> OTHER INFORMATION: The letter "y" stands for t or c.

<400> SEQUENCE: 29
cctccacctt ygacgctggg g                                              21

<210> SEQ ID NO 30
<211> LENGTH: 21
<212> TYPE: DNA

```
<213> ORGANISM: Homo sapiens
<220> FEATURE:
<223> OTHER INFORMATION: Glutamate-ammonia ligase (glutamine synthase)
<220> FEATURE:
<223> OTHER INFORMATION: The letter "s" stands for g or c.

<400> SEQUENCE: 30
tcgcggccta sctttacccg c                                              21

<210> SEQ ID NO 31
<211> LENGTH: 21
<212> TYPE: DNA
<213> ORGANISM: Homo sapiens
<220> FEATURE:
<223> OTHER INFORMATION: Glutamate-ammonia ligase (glutamine synthase)
<220> FEATURE:
<223> OTHER INFORMATION: The letter "y" stands for t or c.

<400> SEQUENCE: 31
tcgatggctc yagtacttta c                                              21

<210> SEQ ID NO 32
<211> LENGTH: 21
<212> TYPE: DNA
<213> ORGANISM: Homo sapiens
<220> FEATURE:
<223> OTHER INFORMATION: Glutamate-ammonia ligase (glutamine synthase)
<220> FEATURE:
<223> OTHER INFORMATION: The letter "m" stands for a or c.

<400> SEQUENCE: 32
gtagcgccag mctacgcatt c                                              21

<210> SEQ ID NO 33
<211> LENGTH: 21
<212> TYPE: DNA
<213> ORGANISM: Homo sapiens
<220> FEATURE:
<223> OTHER INFORMATION: Glutamate-ammonia ligase (glutamine synthase)
<220> FEATURE:
<223> OTHER INFORMATION: The letter "r" stands for g or a.

<400> SEQUENCE: 33
caaggaagtg rttcttagat g                                              21

<210> SEQ ID NO 34
<211> LENGTH: 21
<212> TYPE: DNA
<213> ORGANISM: Homo sapiens
<220> FEATURE:
<223> OTHER INFORMATION: Glutamate-ammonia ligase (glutamine synthase)
<220> FEATURE:
<223> OTHER INFORMATION: The letter "r" stands for a or g.

<400> SEQUENCE: 34
gcctaacata araaaaaaaa a                                              21

<210> SEQ ID NO 35
<211> LENGTH: 21
<212> TYPE: DNA
<213> ORGANISM: Homo sapiens
<220> FEATURE:
<223> OTHER INFORMATION: Fanconi anemia complementation group C
<220> FEATURE:
<223> OTHER INFORMATION: The letter "s" stands for g or c.

<400> SEQUENCE: 35
tggcgagggg scttgacggc g                                              21
```

<210> SEQ ID NO 36
<211> LENGTH: 21
<212> TYPE: DNA
<213> ORGANISM: Homo sapiens
<220> FEATURE:
<223> OTHER INFORMATION: The letter "r" stands for g or a.

<400> SEQUENCE: 36
gcaccggaag raggcgctga c                                      21

<210> SEQ ID NO 37
<211> LENGTH: 21
<212> TYPE: DNA
<213> ORGANISM: Homo sapiens
<220> FEATURE:
<223> OTHER INFORMATION: The letter "s" stands for c or g.

<400> SEQUENCE: 37
ttgagcccaa stgcttggac g                                      21

<210> SEQ ID NO 38
<211> LENGTH: 21
<212> TYPE: DNA
<213> ORGANISM: Homo sapiens
<220> FEATURE:
<223> OTHER INFORMATION: The letter "y" stands for c or t.

<400> SEQUENCE: 38
actgcttgga ygccttccca a                                      21

<210> SEQ ID NO 39
<211> LENGTH: 21
<212> TYPE: DNA
<213> ORGANISM: Homo sapiens
<220> FEATURE:
<223> OTHER INFORMATION: The letter "w" stands for t or a.

<400> SEQUENCE: 39
acctgtgttc wcaaagatgg c                                      21

<210> SEQ ID NO 40
<211> LENGTH: 21
<212> TYPE: DNA
<213> ORGANISM: Homo sapiens
<220> FEATURE:
<223> OTHER INFORMATION: The letter "s" stands for c or g.

<400> SEQUENCE: 40
gctgcccagg stgtgcagcg c                                      21

<210> SEQ ID NO 41
<211> LENGTH: 21
<212> TYPE: DNA
<213> ORGANISM: Homo sapiens
<220> FEATURE:
<223> OTHER INFORMATION: The letter "y" stands for c or t.

<400> SEQUENCE: 41
aacatcccct yccatcatta c                                      21

<210> SEQ ID NO 42
<211> LENGTH: 21
<212> TYPE: DNA
<213> ORGANISM: Homo sapiens
<220> FEATURE:

-continued

```
<223> OTHER INFORMATION: The letter "y" stands for c or t.

<400> SEQUENCE: 42
ctgcctggcc yctcgcctgt g                                           21

<210> SEQ ID NO 43
<211> LENGTH: 21
<212> TYPE: DNA
<213> ORGANISM: Homo sapiens
<220> FEATURE:
<223> OTHER INFORMATION: The letter "r" stands for g or a.

<400> SEQUENCE: 43
cggtgagacc rttgcccgct g                                           21

<210> SEQ ID NO 44
<211> LENGTH: 21
<212> TYPE: DNA
<213> ORGANISM: Homo sapiens
<220> FEATURE:
<223> OTHER INFORMATION: The letter "w" stands for a or t.

<400> SEQUENCE: 44
ctctgaagac wtggagatac t                                           21
```

INHIBITORS OF ALTERNATIVE ALLELES OF GENES ENCODING PRODUCTS THAT MEDIATE CELL RESPONSE TO ENVIRONMENTAL CHANGES

BACKGROUND

This invention is concerned with the field of treatment of proliferative disorders, including malignant and nonmalignant proliferative diseases.

The following information is provided to assist the understanding of the reader, none of that information is admitted to be prior art to the present invention.

The treatment of cancer is one of the most heavily investigated areas in biomedical research today. Although many anticancer drugs have been and continue to be discovered, there remains the immense problem of developing drugs that will be specifically toxic to cancer cells without killing normal cells and causing toxic, often permanent, damage to vital organs or even death. One common measure of the clinical usefulness of any anticancer drugs is its therapeutic index: the ratio of the median lethal dose ($LD_{50}$) to the median effective dose ($ED_{50}$) of the drug. With some cancer therapeutics this ratio is in the range of 2–4, indicating a high risk of toxic side effects to the patient. Indeed, most anticancer drugs are associated with a high incidence of adverse drug events. The poor therapeutic index of most anticancer drugs not only limit the clinical efficacy of these drugs for the treatment of cancer, but limits their usefulness for treating many non-malignant, proliferative disorders.

A strategy for the development of anticancer agents having a high therapeutic index is described in Housman, International Application PCT/US/94 08473 and Housman, INHIBITORS OF ALTERNATIVE ALLELES OF GENES ENCODING PROTEINS VITAL FOR CELL VIABILITY OR CELL GROWTH AS A BASIS FOR CANCER THERAPEUTIC AGENTS, U.S. Pat. No. 5,702,890, issued Dec. 30, 1997, which are hereby incorporated by reference in their entireties. As further described below, the method involves the identification of genes essential to cell growth or viability which are present in two or more allelic forms in normal somatic cells of a cancer patient and which undergo loss of heterozygosity in a cancer. Treatment of a cancer in an individual who is heterozygous with an allele specific inhibitor targeted to the single allele of an essential gene which is present in a cancer will inhibit the growth of the cancer cells. In contrast, the alternative allele present in non-cancerous cells (which have not undergone loss of heterozygosity) is able to express active product which supplies the essential gene function, so that the normal cells can survive and/or grow.

Cancer cells from an individual almost invariably undergo a loss of genetic material (DNA) when compared to normal cells. Frequently, this deletion of genetic material includes the loss of one of the two alleles of genes for which the normal somatic cells of the same individual are heterozygous, meaning that there are differences in the sequence of the gene on each of the parental chromosomes. The loss of one allele in the cancer cells is referred to as "loss of heterozygosity" (LOH). Recognizing that almost all, if not all, varieties of cancer undergo LOH, and that regions of DNA loss are often quite extensive, the genetic content of deleted regions in cancer cells was evaluated and it was found that genes essential for cell viability or cell growth are frequently deleted, reducing the cancer cell to only one copy. Further investigation demonstrated that the loss of genetic material from cancer cells sometimes results in the selective loss of one of two alleles of a certain essential gene at a particular locus or loci on a particular chromosome.

Based on this analysis, a therapeutic strategy for the treatment of cancer was developed, which will produce agents characterized by a high therapeutic index. The strategy includes: (1) identification of genes that are essential for cell survival or growth; (2) identification of common alternative alleles of these genes; (3) identification of the absence of one of these alleles in cancer cells due to LOH and (4) development of specific inhibitors of the single remaining allele of the essential gene retained by the cancer cell, but not the alternative allele.

SUMMARY OF THE INVENTION

While the patent identified above describes a beneficial approach to cancer therapy using allele specific inhibitors of essential genes, it was found in the present invention that a new class of genes can also provide advantageous treatment methods for cancer or other proliferative disorders involving loss of heterozygosity, based on genetic differences in one or more of those genes between normal somatic cells and cells of the proliferative disorder. While the following discussion is principally presented in the context of cancer treatment, those skilled in the art will undertand that non-malignant proliferative disorders can instead be involved, as described in Housman et al., TARGET GENES FOR ALLELE-SPECIFIC DRUGS, attorney docket number 232/116, filed the same day as the present application, which is hereby incorporated by reference in its entirety including drawings.

It was recognized that environmental factors can cause certain genes to be essential that are not essential under other conditions (including usual in vivo and culture conditions). For example, certain genes involved in intermediary metabolism are not essential if the cell or organism is supplemented with high concentrations of a particular nutrient or chemical entity, but if that nutrient or chemical entity is absent or present at low levels, the gene product is essential. In another example, the administration of a drug that inhibits one or more functions within the cell can cause other functions to be essential that are not essential in the absence of the drug. In another example, subjecting a cell to harsh physical agents, such as radiation, can cause certain genes to be essential that are not essential under normal conditions. Such genes are essential under certain conditions associated with the therapy of cancer. The demonstration that such genes are present in the population in more than one allelic form and are subjected to loss of heterozygosity in cancer or noncancer proliferative disorders makes such genes targets for allele specific drugs for the treatment of such disorders.

It was found that such genes, similar to generally essential genes, are frequently deleted due to LOH in cells of proliferative disorders such as cancers.

Thus, the present invention is directed to the use of genes which are referred to as conditionally essential genes as targets or as indicators of an appropriate antiproliferative treatment. Such conditionally essential genes are those which are necessary or beneficial to the growth, proliferation, or survival of a cell under particular environmental conditions, but not under normal in vivo conditions. Treatment methods involving such genes can provide enhanced sensitivity of cancer cells to a variety of different anti-proliferative treatments, including radiation and administration of various compounds. Unless otherwise indicated, the term "essential" includes both strictly essential and beneficial to cell growth or survival.

A gene is said to be "conditionally essential" if it is essential for cell survival or proliferation in a specific environmental condition caused by the presence or absence of specific environmental constituents, pharmaceutical agents, including small molecules or biologicals, or physical factors such as radiation, or if the gene enhances the growth or survival of the cell under such conditions by at least 2-fold, preferably by at least 4-fold, and more preferably by at least 6-fold, 10-fold or even more.

Cancer cells, as well as cells from a number of different non-malignant proliferative disorders, from an individual almost invariably undergo a loss of genetic material (DNA) when compared to normal cells. Frequently, this deletion of genetic material includes the loss of one of the two alleles of genes for which the normal somatic cells of the same individual are heterozygous, meaning that there are differences in the sequence of the gene on each of the parental chromosomes. The loss of one allele in the cancer cells is referred to as "loss of heterozygosity" (LOH). Recognizing that almost all, if not all, varieties of cancer undergo LOH, and that regions of DNA loss are often quite extensive, the genetic content of deleted regions in cancer cells was evaluated and it was found that a variety of different conditionally essential genes are frequently deleted, reducing the cancer cell to only one copy. In this context, the term "deleted" refers to the loss of one of two copies of a chromosome or sub-chromosomal segment. Further investigation demonstrated that the loss of genetic material from cancer cells sometimes results in the selective loss of one of two alleles of a particular gene at a particular locus or loci on a particular chromosome.

In a first aspect, the invention provides a method for identifying an inhibitor potentially useful for treatment of cancer or other proliferative disorder. The nhibitor is active on a conditionally essential gene, and the gene is subject to loss of heterozygosity in a cancer. The method includes identifying at least two alleles of a said gene which differ at at least one sequence variance site and testing a potential allele specific inhibitor to determine whether the potential inhibitor is active on at least one but less than all of the identified alleles. If the potential inhibitor inhibits expression of at least one but less than all of the alleles or reduces the level of activity of a product of at least one but less than all of the alleles, this indicates that the potential allele specific inhibitor is, in fact such an allele-specific inhibitor inhibitor.

In preferred embodiments of this and the various aspects described below, the conditionally essential gene is one of the exemplary genes presented in the table of conditionally essential genes or in the examples.

In this context, a "gene" is a sequence of DNA present in a cell that directs the expression of a "biologically active" molecule or "gene product", most commonly by transcription to produce RNA ("RNA transcript") and translation to produce protein ("protein product"). Both RNA and protein may undergo secondary modifications such as those induced by reacting with other constituents of the cell which are also recognized as gene products. The gene product is most commonly a RNA molecule or protein, or a RNA or protein that is subsequently modified by reacting with, or combining with, other constituents of the cell. Such modifications may result, for example, in the modification of proteins to form glycoproteins, lipoproteins, and phosphoproteins, or other modifications known in the art. RNA may be modified by complexing with proteins, polyadenylation, or splicing.

The term "gene product" refers to any product directly resulting from transcription of a gene. In particular this includes partial, precursor, and mature transcription products (i.e., RNA), and translation products with or without further processing, such as lipidation, phosphorylation, glycosylation, or combinations of such processing (i.e., polypeptides).

The term "target gene" refers to a gene where the gene, its RNA transcript, or its protein product are specifically inhibited or potentially inhibited by a drug. In references herein to genes or alleles, the term "encoding" refers to the entire gene sequence, including both coding and non-coding sequences unless clearly indicated otherwise.

The term "allele" refers to one specific form of a gene within a cell or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". The term "alternative allele", "alternative form", or "allelic form" refers to an allele that can be distinguished from other alleles by having distinct variances at at least one, and frequently more than one, variant site within the gene sequence.

It is recognized in the art that variances occur in the human genome at approximately one in every 100–500 bases. At most variant sites there are only two alternative variances, wherein the variances involve the substitution of one base for another or the insertion/deletion of a short gene sequence. Within a gene there may be several variant sites. Alternative alleles can be distinguished by the presence of alternative variances at a single variant site, or a combination of several different variances at different sites. In this invention, inhibitors targeted to a specific allelic form or subset of the allelic forms of a gene can be targeted to a specific variance in a selected variant site, or to an allele comprised of a set of variances at different sites. In most but not all cases, the target specificity is based on a nucleotide or amino acid change at a single variance site.

The term "proliferative disorder" refers to various cancers and disorders characterized by abnormal growth of somatic cells leading to an abnormal mass of tissue which exhibits abnormal proliferation, and consequently, the growth of which exceeds and is uncoordinated with that of the normal tissues. The abnormal mass of cells is referred to as a "tumor", where the term tumor can include both localized cell masses and dispersed cells, The term "cancer" refers to a neoplastic growth and is synonymous with the terms "malignancy", or "malignant tumor". The treatment of cancers and the identification of anticancer agents is the concern of particularly preferred embodiments of the aspects of the present invention. Other abnormal proliferative diseases include "nonmalignant tumors", and "dysplastic" conditions including, but not limited to, leiomyomas, endometriosis, benign prostate hypertrophy, atherosclerotic plagues, and dysplastic epithelium of lung, breast, cervix, or other tissues. Drugs used in treating cancer and other non-cancer proliferative disorders commonly aim to inhibit the proliferation of cells and are commonly referred to as antiproliferative agents.

"Loss of heterozyhosity", "LOH", or "allele loss" refers to the loss of one of the alleles of a gene from a cell or cell lineage previously having two alleles of that gene. Normal cells contain two copies of each gene, one inherited from each parent. When these two genes differ in their gene sequence, the cell is said to be "heterozyhous". The term heterozygous indicates that a cell contains two different allelic forms of a particular gene and thus indicates that the allelic forms differ at at least one sequence variance site. When one allele is lost in a cell, that cell and its progeny cells, comprising its cell lineage, become "hemizygous" for that gene or "partially hemizygous" for a set of genes, and heterozygosity is lost. LOH occurs in all cancers and is a common caracteristic or non-malignant, proliferative disorder. In general, many different genes will be affected by loss of heterozygosity in a cell which undergoes loss of heterozygosity. In many cancers 10–40% of all the genes in the human genome (there are estimated to be 60,000–100,000 different genes in the genome will exhibit LOH. In the context of this invention, these terms refer preferably to loss of heterozgosity of a gene which has a particular sequence variance in normal somatic cells of an individual such that there is loss of heterozygosity with respect to that particular sequence variance. Also preferably, these terms refer to loss of heterozygosity of a particular sequence variance that is recognized by an inhibitor that will inhibit one allele of the gene present in normal cells of the individual, but not a alternative allele.

The phrase "inhibitor of a conditionally essential gene" means that the inhibitor compound acts to reduce the activity of a product of a conditionally essential gene. Such a reduction in activity can be performed, for example, at a nucleic acid level or at a polypeptide level and can involve direct interaction on the gene or a product of the gene or on a functionally related molecule in a manner which reduces the activity of a product of the particular gene. As the gene is conditionally essential, the inhibition will inhibit cell proliferation or survival under conditions where the function of the gene product is needed by the cell, or under conditions where the gene product enhances the growth or survival of the cell even if the gene product is not strictly essential in those condtions.

In a related aspect, the invention provides an inhibitor potentially useful for treatment of cancer. The inhibitor is active on an allelic form of a conditionally essential gene which has at least two alternative alleles in a population, and the inhibitor targets at least one but less than all of those alternative alleles. In connection with allele specific inhibitors, in preferred embodiments, the specificity of the inhibitor is determined by a single variance site, either directly by targeting the inhibitor to the nucleotide sequence at or near the variance site at the nucleic acid level, or by targeting to at the polypeptide level based on changes to the polypeptide created by the particular sequence at a single variance site.

In another related aspect, the invention provides a pharmaceutical composition which includes at least one allele specific inhibitor targeting at least one but less than all allelic forms of a conditionaly essential gene in a population, along with a pharmaceutically acceptable carrier or excipient. Thus, the composition includes an allele specific inhibitor as described for the above aspects. Such carriers or excipients are known in the art and some commonly used carriers are described in the Detailed Description below. Also in preferred embodiments the composition includes two, three, or more allele specific inhibitors, and may also include a pharmaceutically acceptable carrier. In other preferred embodiments, the composition includes at least one allele specific inhibitor and another antineoplastic agent, which need not be an allele specific inhibitor. The embodiments of this aspect may also optionally include diluents and/or other components as are commonly used in pharmaceutical compositions or formulations. In embodiments having a plurality of allele specific inhibitors, the inhibitors may target a plurality of different variances of a single target essential gene, or may target sequence variances of a plurality of different essential genes or combinations thereof.

Yet another related aspect concerns a method for producing an inhibitor potentially useful for cancer treatment, where the inhibitor is as described above. The method involves identifying a conditionally essential gene that has alternative allelic forms in a noncancerous cell, where one of those alternative allelic forms is deleted in a cancer cell; screening to identify an inhibitor which inhibits at least one but less than all of those alleles; and synthesizing that inhibitor in an amount sufficient to produce a therapeutic effect when administered to a patient suffering from a cancer in whom cancerous cells have only an allele of said gene inhibited by said inhibitor and in whom normal somatic cells are heterozygous for that gene and contain an allelic form not inhibited by said inhibitor. The cancer cells have only one allele due to LOH.

In another aspect, the invention concerns a method for preventing the development of cancer in a patient having a precancerous condition by administering to the patient a therapeutic amount of an allele specific inhibitor targeted to an allele of a conditionally essential gene present in cells of a pecancerous condition. The normal somatic cells of that patient are heterozygous for the first gene. The inhibitor is active on at least one but less than all allelic forms of the gene present in a population and targets only one allelic form present in normal somatic cells of the patient. Cells of the precancerous condition have undergone LOH of that first gene. In preferred embodiments, the cells of the precancerous condition are not clonal from a single cell. In this case, the method also includes serially administering to the patient at least one additional allele specific inhibitor which targets a different allele of a conditionally essential gene or an essential gene than is targeted by the first allele specific inhibitor. The different allele may be a different allele of the first gene or an allele of a different gene. The patient is heterozygous for each targeted gene and each targeted gene has undergone LOH in cells of said precancerous condition.

The invention also concerns a method for treating a patient suffering from a cancer, where the patient is heterozygous for a conditionally essential gene. The method inlcudes subjecting cells of the cancer to conditions such that the gene is essential; and administering to the patient a therapeutic amount of an allele specific inhibitor active on at least one but less than all allelic forms of the gene present in a population. The allele specific inhibitor inhibits only one allelic form of the gene present in normal somatic cells of the patient, and only one allelic form, a targeted allele, of the gene is present in cancer cells in the patient.

In preferred embodiments the method also inlcudes the steps of determining whether non-cancerous cells of the patient are heterozygous for a particular conditionally essential gene; or determining whether cancerous cells of said patient have only one allele of said particular gene; or both.

Also included is a method of inhibiting growth of a cell by subjecting the cell to conditions such that the gene is essential and administering at least one inhibitor active on an allele of the conditionally essential gene. The inhibitor is less active on at least one other allele of said gene.

The invention also includes a method of identifying a potential patient for treatment with an inhibitor which is active on at least one but less than all alleles of a conditionally essential gene, where the patient is suffering from a cancer by identifying a patient whose normal somatic cells are heterozygous for a particular conditionally essential gene. If the patient is heterozygous for that gene, this indicates that the patient is a potential patient for treatment with such an allele specific inhibitor, because it allows the cancer cells to be differentially affected by the inhibitor where the cancer cells have undergone LOH of that gene. Thus, in preferred embodiments, the method also inlcudes determining whether cancer cells in the patient contain only a single allele of said gene, thereby demonstrating that the allele specific inhibitor will differentially affect the cancer cells by targeting the only allele of the gene present in those cells. In preferred embodiments, targeting of the allele of the gene in the cancer cells increases the sensititity of those cells to the administration of an antineoplastic treatment, e.g., a convention anticancer treatment such as radiation or a cytotoxic drug.

Likewise, in a related aspect, the invention provides a method of identifying a potential patient for treatment with an inhibitor as in the preceding aspect by determining whether cancer cells in the patient have undergone LOH of a such a gene. If the cells have undergone LOH of that gene, then the patient is a potential patient for said treatment because it potentially allows allele specific targeting of the remaining allele of the gene in the cancer cells.

Determinations of essential gene heterozygosity and tumor cell LOH may be performed by a variety of methods, such as direct sequencing of known sequence variance sites and probe hybridization with variance specific probes. Thus, in accord with the above identification methods, in another aspect, the invention provides a nucleic acid probe at least 12 nucleotides in length which is perfectly complementary to a portion of a first allelic form of a conditionally essential gene.

That portion includes a sequence variance site, and the probe hybridizes under stringent hybridization conditions to said portion and not to a corresponding portion of a second allelic form of the gene which has at least one different nucleotide at the sequence variance site. Thus, the stringent hybridization conditions are selective hybridization conditions. Thus, the invention provides a nucleic acid probe at least 12, and preferably 15, 17, or 20 nucleotides in length, but preferably not more than 30 nucleotides, which will hybridize to a portion of a first allelic form of a conditionally essential gene under specified hybridization conditions and not to a second allelic form under those hybridization conditions where the first and second allelic forms have a sequence variance within the complementary sequence. Preferably the probe is perfectly complementary to a portion of the first allelic form which includes a sequence variance site. The probe hybridizes under stringent hybridization conditions to the portion of the first allelic form and not to the corresponding portion of the second allelic form. This means that the probe does not bind to the second allelic form to an extent which prevents identification of the preferential specific binding to the first allelic form. The thermodynamics of the probe hybridization can be predicted to maximize the desired differential hybridization, providing optimization for probe length, sequence, structural modifications, and modifications to hybridization conditions.

The invention also provides nucleic acid probes or primers adjacent to the site of a variance that can be used to amplify a sequence containing the variant position to determine which variance is present at that position. Such probes or primers can readily be designed based on the sequences provided in the corresponding database sequence entry or otherwise determined. The method of determining the variance can involve allele specific hybridization, sequencing or analysis of the amplified fragment by mass spectroscopy, SSCP, gene sequence database analysis, capillary electrophoresis, bindase/resolvase systems, or other methods known in the art. In a preferred embodiment, the amplified sequence spans more than one variant position and the method used for determining the variances identifies which variances are present at each position and combinations of variances that are present on each allele.

In still another aspect, not requiring the use of allele specific inhibitors, but still utilizing information about sequence variance or allelic differences between normal somatic cells and cancer cells in a patient, the invention provides a method for selecting a patient for treatment with an antiproliferative treatment. The method includes the following steps: determining whether normal somatic cells in a potential patient are heterozygous for an essential or conditionally essential gene, where a first allelic form of the gene is more active than a second allelic form, and where a reduction in the activity of the gene in a cell increases the sensitivity of that cell to an antiproliferative treatment; and determining whether cancer cells from the patient have only the second allelic form of the gene. If the somatic cells are heterozygous and the cancer cells have only the second allelic form, this indicates that the patient is suitable for treatment with the antiproliferative treatment because the cancer cells will be more sensitive to the antiproliferative treatment. In preferred embodiments, the antiproliferative treatment is radiation or administration of a cytotoxic drug.

In a related aspect, the differences between the normal somatic cells and the cancer cells in a patient are used in a method for selecting an antiproliferative treatment for a patient suffering from a cancer. This method involves determining whether there will be a differential effect of the prospective treatment on the cancer cells as compared to the normal cells based on a differential response of the cancer cells due the the presence in the cancer cells of only the less active form of a conditionally essential gene which is present in two alternative allelic forms with differing activities in the somatic cells. The method thus involves determining whether normal somatic cells in a potential patient are heterozygous for an essential or conditionally essential gene which reduces the sensitivity of cells to an antiproliferative treatment. As noted, a first allelic form of the gene is more active than a second allelic form, and a reduction in the activity of the gene in a cell increases the sensitivity of that cell to the prospective antiproliferative treatment; and determining whether cancer cells of said patient have only the second, less active, allelic form of the gene. If these factors are present, this indicates that the proposed treatment is suitable for that patient.

In preferred embodiments of above aspects, a conventional therapy acts on a protein or other molecular target in the same pathway as the allele specific inhibitor. As an example, the antineoplastic drug hydroxyurea, which inhibits ribonucleotide reductase (RR), can be used in conjunction with an allele specific inhibitor of RR subunit M1 or M2 or or another gene that encodes a product important in nucleotide synthesis. Similarly, the antiproliferative drug methotrexate inhibitos the enzyme dihydrofolate reductase (DHFR), and can be used with allele specific inhibitors of DHFR that would result in a differential methotrexate effect on cancer tissues compared to normal proliferating tissues. Alternatively, methotrexate can be used with allele specific inhibitors of other genes important in folate metabolism to achieve an enhanced cancer cell specificity for methotrexate. Similarly, the anticancer drug 5-flurouracil and related compounds can be administered together with an allele specific inhibitor of thymidylate synthase (TS) in a patient heterozygous for TS and with LOH at the TS gene in proliferating cells, e.g., cancer cells. Alternatively, an allele specific inhibitor of 5-FU degradation or metabolism can be administered with 5-FU. For example, the enzyme dihydropyrimidine dehydrogenase, which catalyzes the first and rate limiting step in 5-FU catabolism would have the effect of potentiating 5-FU action in cancer cells due to their lesser ability to metabolically inactivate 5-FU. One skilled in the art will readily recognize that similar methods can be used with other conditionally essential genes, incuding specific genes listed in the table of conditionally essential genes.

Some conditionally essential genes occur in active and less active, or nearly inactive alleleic forms. Further, some cancer patients are heterozygous for active and less active forms in their normal tissues, but due to LOH, their cancer cells contain only the less active allelic form. As describe above, such patients can be identified by a diagnostic test of their normal cells and cancer cells. Such a test will identify which patients should be treated with a specific treatment, such as a particular drug or radiation treatment or other treatment. Such a therapy, which is not allele specific, would nonetheless have cancer specific effects due to the LOH-determined difference in the ability of the cancer cells to respond to the cytotoxic or cytostatic effects of therapy.

For example, patients with Ataxia Telangiectasia are homozygous for mutant alleles of the ATM gene. Such indivduals are hypersensitive to radiation therapy or radiomimetic drugs. Heterozygotes for normal and mutant ATM are normal and have been estimated to account for 0.5–1% of the North American population, but, due to an increased risk of caner, may account for up to 5% of some cancers, for example, breast cancer. The ATM gene maps to chromosome 11q23, a region frequently affected by LOH in breast and other cancers. In breast cancers arising in ATM heterozygotes in which the more active (normal) ATM allele is lost in cancer tissue due to LOH, treatment with radiation or radiomimetic drugs would be differentially toxic to cancer cells. It has been shown that ATM heterozygotes are less sensitive to such treatments than ATM mutant (less active) homozygotes. Such use of an LOH diagnostic procedure to select appropriate antineoplastic therapy represents a change from the current procedures which are based solely on tissue origin, grade, and stage of cancer.

In such an approach, preferably the difference in activity between more active and less active allelic forms is at least 2×, more preferably at least 3×, 4×, or 5×, and most preferably at least 6×, 10×, or even more.

Exemplary genes described herein are shown to contain numerous sequence variances which are present in human populations. While some sequence variances and alleles are common throughout diverse human populations, it is recognized in the art that the allele frequency of different genes will vary in different populations. For example, allele frequencies have been shown to differ between populations comprised of individuals of different races, populations comprised of individuals from different countries, populations comprised of individuals from different regions, populations comprised of individuals with common ethnic background, and even populations comprised of individuals from different religions. Alleles that are common in one population, may be rare in another. While the allele frequency of any particular gene may vary in different populations, preferably a target gene is one such that at least 0.1%, 0.5%, 1% or 5% of a population is heterozygous for the sequence variance, preferably so that at least 10% or 20%, more preferably at least 30%, and most preferably at least 40% are heterozygous in a specific population that may be treated with inhibitors to treat cancer or other proliferative disorder in that population. Once a specific variance is identified in a certain gene, the allele frequency in any specific population can be easily determined using methods known in the art including the use of allele-specific hybridization probes, sequencing, or specific PCR reactions.

In this regard, "population" refers to a geographically, ethnically, or culturally defined group of individuals, or a group of individuals with a particular disease or a group of individuals that have proliferative diseases that may be treated by the present invention. Thus, in most cases a population will preferably encompass at least ten thousand, one hundred thousand, one million, ten million, or more individuals, with the larger numbers being more preferable. In special circumstances, diseases will occur with high frequency in specific geographical regions or within specific familial, racial, or cultural groups, and a relevant population may usefully be considered to be a smaller group.

In the context of this invention, an alternative allele, or other reference to an appropriate target for the inhibitors of this invention refers to a form of a gene which differs in base sequence from at least one other allele or allelic form of the same gene. Usually, though not necessarily, the allelic forms of a gene will differ by, at most, several bases and may have only a single base difference (i.e., a single sequence variance). The allelic forms, however, are ones which contain at least one sequence variance which appears in somatic cells of a population at an appreciable frequency, such that preferably at least 0.1%, 0.5%, or 1%, more preferably at least 5%, still more preferably at least 10%, and most preferably at least 20% of the population are heterozygous for that specific sequence variance. This advantageously allows the convenient identification of potential patients, because an appreciable fraction of the population, and therefore also of the cancer patients will be heterozygous for sequence variances of the specific gene. In the context of this invention, different alleles need not result in different observable phenotypes under normal conditions. Preferably, a particular sequence variance produces no phenotypic effect on the physical condition of an individual having that variance until the variance or allele is targeted by an allele specific inhibitor under conditions such that the function of the gene product is needed.

In connection with allele specific inhibitors and the methods of this invention, the terms "allelic form" or "alternative form of the target gene" or "sequence variance within the target gene" refer to either or both of the gene or a product of that gene including the RNA transcript or protein product. Thus, a particular inhibitor may act in an allele specific manner (which will often be variance specific) at any of those levels and preferably the inhibitor is targeted to a particular sequence variance of the specific allelic form.

As indicated above, two different allelic forms of a gene will have at least a one nucleotide difference in the nucleotide sequence of the gene. The difference can be of a variety of different types, including base substitution, single nucleotide insertion or deletion, multiple nucleotide insertion or deletion, and combinations of such differences. Thus, two allelic forms are sequence variants and will have at least one sequence variance, which refers to the sequence difference, between the allelic forms. However, there may also be more than one sequence variae between two allelic forms. The location of a sequence variance in a gene sequence is a "sequence variance site." This description applies to both the DNA and RNA sequences, and similarly applies to a polypeptide sequence encoded by the gene, differences in the amino acid sequence of the polypeptide, and the location in the polypeptide chain of the sequence differences. As a particular gene may have more than one sequence variance site, more than two allelic forms may and often will exist in a population.

Sequence variances can involve a difference in the sequence in which any of the four bases: adenine, guanine, thymidine (uracil in the context of RNA), or cytosine are substituted with another of the four bases or a change in the length of the sequence. Different classes of variances are recognized in the art. "Deletions" are variances in which one or more bases are missing from the sequence. "Insertions" are variances in which one or more bases are inserted into the sequence. It will be evident that the terms deletion and insertion refer to the variance in one sequence relative to another. "Transitions" are variances that involve substitution of one purine for the other or one pyrimidine for the other. "Transversions" are variances that involve substitution of a purine for a pyrimidine or a pyrimidine for a purine. Certain sequence variances can interfere with the normal function of the gene or its gene product and can be associated with disease; such variances are commonly referred to as mutations. Most variances present in human populations are not associated with disease and are "normal" variants of the gene; such variances are commonly referred to as polymorphisms.

This invention provides inhibitors which are specific for at least one, but not all, allelic forms of a gene that encodes a gene product essential to cell growth or cell viability, for genes belonging to the specified categories of genes. The inhibitor may be active on the gene or gene product including the RNA transcript, protein product, or modifications thereof. Exposure to the inhibitor inhibits proliferation or kills cells which have undergone LOH of genes that are not inhibited by the drug and contain only an allelic form of the essential gene, its RNA transcript, or its protein product against which the inhibitor is targeted, under the appropriate altered conditions. Normal cells which contain two alternative alleles of the target genes, one of which is not inhibited by the specific inhibitor, are spared from the effects of the inhibitor because the remaining activity of the allele which is not inhibited by the inhibitor is adequate to permit continued cell viability and growth under the relevant altered conditions.

In many, or even most, cases an allele specific inhibitor discriminates between two allelic forms due to a particular single sequence variance between the allelic forms of the target gene. For example, ribozymes which target a single sequence variance site will preferentially cleave only one of the sequence variants for a particular single nucleotide variance. In this case, sequence variances at other sites will generally not affect the cleavage. Thus, in preferred embodiments of the above aspects, an allele specific inhibitor discriminates between two allelic forms by discriminating a single sequence variance. As previously indicated, inhibitors can be targeted to either the nucleic acid or a polypeptide (where a nucleotide change results in an amino acid change). In particular embodiments, the allele specific inhibitor will recognize more than one linked sequence variances within a specific allele.

An "allele specific inhibitor" or "variance specific inhibitor" is a drug or inhibitor that inhibits the activity of one alternative allele of a gene to a greater degree than at least one other alternative allele. The difference in activity is commonly determined by the dose or level of a drug required to achieve a quantitative degree of inhibition. A commonly used measure of activity is the IC50 or concentration of the drug required to achieve a 50% reduction in the measured activity of the target gene. Preferably an allele specific inhibitor will have at least twice the activity on the target allelic form than on a non-target allelic form, more preferably at least 5 times, still more preferably at least 10 times, and still more preferably at least 50 times, and most preferably at least 100 times. This can also be expressed as the sensitivities of the different allelic forms to the inhibitor. Thus, for example, it is equivalent to state that the target allelic form is most preferably at least 100 times as sensitive to the inhibitor as a non-target allelic form. The activity of an inhibitor can be measured either in vitro or in vivo, in assay systems that reconsitute the in vivo system, or in systems incorporating selected elements of the complete biological system. For use in inhibiting cells containing only the target allelic form rather than cells containing at least one non-targeted allelic form, the difference in activity is preferably sufficient to reduce the proliferation rate or survival rate of the cells having only the targeted allelic form to no more than one half of the proliferation rate or survival rate of cells having at least one non-targeted allelic form. More preferably, the fraction is no more than $1/5$ or $1/10$, and still more preferably no more than $1/20$, $1/50$, $1/100$, or even lower.

In the context of this invention, the term "active on an allelic form" or "allele specific inhibitor" or "specific for an allelic form" indicates that the relevant inhibitor inhibits an allele having a particular sequence to a greater extent (preferably $\geq 2\times$) than an allele having a sequence which differs in a particular manner. Thus, for alleles for which a particular base position is identified, the inhibitor has a higher degree of inhibition when a certain base is in the specified position then when at least one different base is in that position. This means that for substitution at a particular base position, at least two of the possible allelic forms differ in sensitivity to an inhibitor. Usually, however, for a specific sequence variance site, the site will be occupied by one of only two bases. Further, if an inhibitor acts at the polypeptide level, and any of three bases may be present at a particular position in a coding sequence but only one of the substitutions results in an amino acid change, then the activity of the inhibitor would be expected to be the same for the two forms producing the same amino acid sequence but different for the form having the different amino acid sequence. Other types of examples can also occur.

The term "less active" indicates that the inhibitor will inhibit growth of or kill a cell containing only the allelic form of a gene on which the inhibitor is more active at concentrations at which it does not significantly inhibit the growth of or kill a cell containing only an allelic form on which the inhibitor is less active.

The term "drug" or "inhibitor" refers to a compound or molecule which, when brought into contact with a gene, its RNA transcript, or its gene product which the compound inhibits, reduces the rate of a cellular process, reduces the level of a cellular constituent, or reduces the level of activity of a cellular component or process. This description is meant to be illustrative of the understanding of the meaning of the term to those skilled in the art and not limiting. Thus, the term generally indicates that a compound has an inhibitory effect on a cell or process, as understood by those skilled in the art. Examples of inhibitory effects are a reduction in expression of a gene product, reduction in the rate of catalytic activity of an enzyme, and reduction in the rate of formation or the amount of an essential cellular component. The blocking or reduction need not be complete, in most cases, for the inhibitor to have useful activity. Thus, in the present invention, "inhibitors" are targeted to genes, their RNA transcript, or their protein product that are essential for cell viability or proliferation. Such inhibitors would have the effect of inhibiting essential functions, leading to loss of cell viability or inhibition of cell proliferation. In preferred embodiments, such inhibitors cause cell death or stop cell proliferation. In preferred embodiments of this invention, inhibitors specifically include a molecule or compound capable of inhibiting one or more, but not all, alleles of genes, their RNA transcript, or their protein product that are essential for cell survival or proliferation. The terms "inhibitor of a gene" or "inhibitor of an allele" as used herein include inhibitors acting on the level of the gene, its gene product, its RNA transcript, its protein product, or modifications thereof and is explicitly not limited to those inhibitors or drugs that work on the gene sequence itself.

Several types of inhibitors are generally recognized in the art. A "competitive" inhibitor is one that binds to the same site on the gene, its RNA transcript or gene product as a natural substrate or cofactor that is required for the action of the gene or gene product, and competitively prevents the binding of that substrate. An "allosteric" inhibitor is one that binds to a gene or gene product and alters the activity of the gene or gene product without preventing binding of a substrate or cofactor. Inhibition can also involve reducing the amount of the gene, RNA transcript, or its protein product, and thus the total amount of activity from the gene in the cell. Such inhibition can occur by action at any of a large number of different process points, including for example by inhibiting transcription or translation, or by inducing the elimination of the gene, its RNA transcript, or its protein product where elimination may involve either degradation of the target or egress or export from the compartment in which it is active and the process of excretion or export. Inhibition can also be achieved by modifying the structure of the target, interfering with secondary modifications, or interfering with cofactors or other ancillary components which are required for its activity. Inhibitors can be comprised of small molecules or polymeric organic compounds including oligopeptides or oligonucleotides.

The term "active on a gene" or "targeted to a gene" indicates that an inhibitor exerts its inhibitory effect in a manner which is preferentially linked with the characteristic properties of a gene, its RNA transcript or its gene product. Such properties include, for example, the nucleotide sequence of the gene or transcribed RNA, the amino acid sequence or post-translational modifications of the protein product, the structural conformation of a protein, or the configuration of a protein or RNA with other cellular constituents (RNA, protein, cofactors, substrates, etc.) required for activity. Thus, in general these terms indicate that the inhibitor acts on the gene, its RNA transcript, its protein product, its gene product, or modifications thereof, or on a reaction or reaction pathway necessarily involving such a gene product to a greater extent than on genes or gene products generally.

A "reduction of the level of activity" of a gene product or allele product refers to a decrease in the functional activity provided by that product. This can be due to any of a variety of direct causes, including for example, a reduction in the amount of a biologically active molecule present, a change in the structure or modifications of normally active molecules to produce inactive or less active molecules, blockage of a reaction in which the product participates, and blockage of a reaction pathway in which the product necessarily participates.

A "therapeutic effect" results, to some extent, in a measureable response in the treated disease or condition. Thus, a therapeutic effect can include a cure, or a lessening of the growth rate or size of a lesion such as a tumor, or an increase in the survival time of treated patients compared to controls, among other possible effects.

The term "therapeutic amount" means an amount which, when administered to a mammal, e.g., a human, suffering from a disease or condition, produces a therapeutic effect.

In preferred embodiments of the above aspects in which an allele specific inhibitor is used to inhibit a cell or to treat a patient, a plurality of different inhibitors may be used. Preferably different inhibitors target a plurality of different variances in a single target gene, or target variances in different target genes, or both. In particular embodiments a plurality of inhibitors is used simultaneously, in others there is serial administration using different inhibitors or different sets of inhibitors in separate administrations, which may be performed as a single set of administrations in which each set of inhibitors is administered once, or in multiple serial administrations in which each set of inhibitors is administered more than once. Such use of multiple inhibitors provides enhanced inhibition, which preferably includes killing, of the targeted cells. The inhibitors of a plurality of inhibitors may target a plurality of alleles of conditionally essential genes or a combination of conditionally essential genes and generally essential genes. In addition, allele specific inhibitors as described can be used in conjunction with other treatments for diseases and conditions, including in conjunction with other chemotherapeutic agents such as other antineoplastic agents.

In preferred embodiments of the above methods and inhibitors involving particular target genes or classes or categories of genes, the inhibitor or potential inhibitor is a ribozyme which is designed to specifically cleave a particular target allelic form of a gene (i.e., a nucleotide sequence such as mRNA).

The ribozyme is designed to cleave the nucleotide (e.g., RNA) sequence at a position in the nucleotide chain of the target allelic form at or near the position of a sequence variance. Usually the ribozyme will have a binding sequence which is perfectly complementary to a target sequence surrounding the sequence variance site. Preferably, the ribozyme does not consist of only ribonucleotides, and therefore includes at least one nucleotide analog or modified linkage. In preferred embodiments the ribozyme has a hammerhead or hairpin motif, but may have other structural motifs as known to those skilled in the art.

The term "ribozyme" refers to a catalytic RNA molecule, including those commonly referred to as hammerhead ribozymes and hairpin ribozymes, generally having an endonuclease activity, but includes catalytic RNA molecules, catalytic DNA molecules (DNAzymes), and derivatives of such molecules unless indicated to the contrary. In particular, as understood by those skilled in the art, ribozymes may incorporate a variety of nucleotide analogs, modified linkages, and other modifications.

In connection with ribozymes, "target sequence" refers to a nucleotide sequence which includes a binding site and a cleavage site for a ribozyme. For use in this invention, preferably a gene having a ribozyme target sequence exists in two allelic forms in normal somatic cells of a patient. The two allelic forms differ in nucleotide sequence within the target sequence, i.e., have a sequence variance within the target sequence.

Also in connection with ribozymes, the term "specifically cleaves" means that a particular ribozyme will cleave a target sequence to a greater extent than it will cleave a different sequence. For allele specific ribozymes, this means that for two allelic forms having a sequence variance in the target sequence, preferably the ribozyme will cleave one of the allelic forms more efficiently than the other. Those skilled in the art will understand that the target discrimination can be provided by base differences within the ribozyme binding sequence of the substrate at or close to the cleavage site.

Similarly, in preferred embodiments the inhibitor or potential inhibitor is an oligonucleotide, e.g, an antisense oligonucleotide, preferably at least partially an oligodeoxyribonucleotide. The antisense oligonucleotide is complementary to a sequence which includes a sequence variance site. Usually, though not necessarily, the antisense oligonucleotide is perfectly complementary to a sequence of the target allelic form which includes a sequence variance site. The antisense oligonucleotide preferably is at least twelve nucleotides, more preferably at least seventeen nucleotides in length. In some cases the antisense oligonucleotide may advantageously be longer, for example, at least 20, 25, or 30 nucleotides in length. Also in preferred embodiments, the oligonucleotide is no longer than 20, 25, 30, 35, 40, or 50 nucleotides The optimal length will depend on a number of factors, which may include the differences in binding free energy of the oligonucleotide to the target sequence as compared to binding to the non-target allelic form, i.e., the non-target sequence variant, or the kinetics of nucleic acid hybridization. The oligonucleotide preferably contains at least one nucleic acid analog or modified linkage. Such complementary oligonucleotides may function in various ways, and those skilled in the art will know how to design the oligonucleotide accordingly. Such functional mechanisms include, but are not limited to direct blocking of transcription of a gene by binding to DNA (e.g., high affinity antisense, including triple helix), direct blocking of translation by binding to MRNA, RNaseH mediated cleavage of RNA or other RNAase mediated cleavage, and binding-induced conformational changes which block transcription or translation or alter the half-life of mRNA. Triple-helix modes of action include the formation of a triple-helical structure between the two strands of genomic DNA and an antisense molecule, i.e., anti-gene strategy, or between an RNA molecule and an antisense oligonucleotide which loops back to contribute two of the three strands of the triple helix, or between an RNA and an antisense where the RNA provides two of the three strands of the triple helix.

The term "oligonucleotide" refers to a chain molecule comprising a plurality of covalently linked nucleotides as recognized in the art. The oligonucleotide preferably has about 200 or fewer backbone units corresponding to nucleotide subunits, more preferably about 100 or fewer, still more preferably about 80 or fewer, and most preferably about 50 or fewer. An oligonucleotide may be modified to produce an oligonucleotide derivative. Unless indicted otherwise the term "oligonucleotide" includes "oligonucleotide derivatives".

A large number of nucleic acid modifications are known in the art which may be used in the nucleic acid molecules of the present invention, thereby producing "nucleic acid derivatives" or "oligonucleotide derivatives". Such modifications can be used, for example, to enhance resistance to degradation by nucleases or to modify functional characteristics such as binding affinity. In preferred embodiments, the ribozyme, antisense oligonucleotide, or other nucleic acid molecule contains at least one modified linkage, including but not limited to phosphorothioate, phosphoramidate, methylphosphonate, morpholino-arbamate, and terminal 5'-5' or 3'-3' linkages. Also in preferred embodiments, the nucleic acid molecule contains at least one nucleotide analog. Such analogs include but are not limited to nucleotides modified at the 2' position of the ribose sugar, e.g., 2'-O-alkyl (e.g., 2'-O-methyl or 2'-methyoxyethoxy) or allyl, 2'-halo, and 2'-amino substitutions, and/or on the base (e.g., C-5 propyne pyrimidines), and analogs which do not contain a purine or pyrimidine base, and includes the use of nucleotide analogs at the terminal positions of a nucleic acid molecule. Preferably a 2'-O-alkyl analog is 2'-O-methyl; preferably a 2'-halo analog is 2'-F.

A specific embodiment of this invention is the use of hybrid oligonucleotides that contain within a linear sequence two different types of oligonucleoide modifications. In a particular embodiment, these modifications are used such that a segment of the oligonucleotide that hybridizes to the sequence variance is RNAase sensitive, but other segments are not RNAase sensitive.

Other modifications may also be used as are known in the art, such as those described in connection with antisense and triple helix in: Crooke & Bennett, 1996, *Annual Rev. Pharm. and Toxicol.* 36:107–129; Milligan et al., 1993, *J. Med. Chem.* 36:1923–1937; Reynolds et al., 1994, *Proc. Nat. Acad. Sci. USA* 91:12433–12437; and McShan et al., 1992, *J. Biol. Chem.* 267–5712–5721, which are hereby incorporated by reference. An additional modification useful for delivery of oligonucleotides is complexation of oligonucleotides with nano-particles, as described in Schwab et al., 1994, *Proc, Nat. Acad. Sci. USA* 91:10460–10464. As described further below, oligonucleotides may be complexed with other components known in the art which provide protection and/or enhanced delivery for the oligonucleotides, and may be useful for either gene delivery or for delivery of non-coding oligonucleotides.

Thus, "derivatives of nucleic acid inhibitors" include modified nucleic acid molecules which may contain one or more of: one or more nucleotide analogs, including modifications i the sugar and/or the base, or modified linkages, base sequence modifications, and insertions or deletions, or combinations of the preceding. Other derivatives are also included as are known in the art.

Similarly, in preferred embodiments the inhibitor or potential inhibitor is an antibody, preferably a monoclonal antibody, which may be complexed or conjugated with one or more other components, or a fragment or derivative of such an antibody. It is recognized in the art that antibody fragments can be produced by cleavage or expression of nucleic acid sequences encoding shortened antibody molecule chains. Such fragments can be advantageously used due to their smaller size and/or by deletion of sites susceptible to cleavage. In addition, derivatives of antibodies can be produced by modification of the amino acid moieties by replacement or modification. Such modification can, for example, include addition or substitution or modification of a side chain or group. Many modifications and biological effects of such modifications are known to those skilled in the art, and may be used in derivatives of antibodies in accord with those biological effects. Such effects can include, for example, increased resistance to peptidases, modified transport characteristics, and ability to carry a ligand or other functional moiety. In preferred embodiments, the antibody is a humanized antibody from a non-human animal, e.g., a humanized mouse or rabbit antibody. Many instances of monoclonal antibodies that distinguish protein differing by a single amino acid are known in the art.

An inhibitor may also be an oligopeptide or oligopeptide derivative. Such peptides may be natural or synthetic amino acid sequences, and may have modifications as described for antibodies above. In general, an oligopeptide will be between about 3 and 50 residues in length, preferably between about 4 and 30, more preferably between about 5 and 20 residues in length.

In other embodiments, the inhibitor is a small molecule, for example, a molecule of one of the structural types used for conventional anticancer chemotherapy.

By "small molecule" or "low molecular weight compound" is meant a molecule having a molecular weight of equal to or less than about 5000 daltons, and more preferably equal to or less than about 2000 daltons, and still more preferably equal to or less than about 1000 daltons, and most preferably equal to or less that about 600 daltons. In other highly preferred embodiments, the small molecule is still smaller, for example less than about 500, 400, or 300 daltons. As well known in the art, such compounds may be found in compound libraries, combinatorial libraries, natural products libraries, and other similar sources, and may further be obtained by chemical modification of compounds found in those libraries, such as by a process of medicinal chemistry as understood by those skilled in the art, which can be used to produce compounds having desired pharmacological properties.

In connection with the gene sequences or subsequences of gene sequences or primer sequences as described herein, the sequences listed under the accession number are believed to be correct. However, the genes can be readily identified and the invention practiced even if one or more of the specified sequences contain a small number of sequence errors. The correct sequence can be confirmed by any of a variety of methods. For example, the sequence information provided herein and/or published information can be used to design probes for identifying and isolating a corresponding mRNA. The mRNA can be reverse transcribed to provide cDNA, which can be amplified by PCR. The PCR products can then by used for sequencing by standard methods. Alternatively, cDNA or genomic DNA libraries can be screened with probes based on the disclosed or published gene sequences to identify corresponding clones. The inserts can then be sequenced as above. If complete sequence accuracy is desired, such accuracy can be provided by redundant sequencing of both DNA strands. Those skilled in the art will recognize that other strategies and variations can also be used to provide the sequence or subsequence for a particular gene.

Other features and advantages of the invention will be apparent from the. following description of the preferred embodiments and from the claims.

BRIEF DESCRIPTION OF THE DRAWINGS

FIG. 1 is a Target Variances by Field Table, which summarizes information on DNA sequence variances in selected genes from the table of genes and proteins vital for cell survival or proliferation in the presence of an altered environment (Table 2).

The heading at the top of each category of genes identifies functional categories of useful conditionally essential genes.

Below the heading is a sentence on 'Validation' which points out that the genes are conditionally essential. Summary information on target gene variances is then listed, with five columns of data.

The first column gives the Variagenics gene ID number, which serves as a cross reference to the Target Variances Table (see below), where more detailed information on variances can be found.

The second column lists gene names. (The GenBank accession number in column 5 may be a more consistent way to identify genes.)

The third column lists the number of variances found to this time. These variances were detected by a variety of experimental and informatics based procedures mentioned herein. Many variances were detected by two independent methods (e.g. informatics based detection and T4 endonuclease VII detection). A molecular description of the variances is provided in the Target Variances Table (see FIG. 2).

The fourth column lists the chromosome location of the target gene, if known. Knowledge of the chromosome location permits assessment of the cancers in which LOH would be expected to affect the target gene.

The fifth column lists the GenBank accession number of the target gene.

FIG. 2 is a Target Variances Table showing molecular details of exemplary variances identified in exemplary target genes. There are six columns in the Table.

The first column gives an arbitrary gene ID number, which serves as a cross reference to the Target Variances by Field Table (see above), where information on gene location and GenBank accession number are provided. After the ID number is a decimal point and then a list of one or more integers (on successive lines), which are the (arbitrary) numbers of the specific variances identified. Between one and 13 variances were identified per target gene. Information on different target genes is separated by dashed horizontal lines.

The second column lists the location of the variance—specifically the number of the nucleotide at which variation was observed. The nucleotide number refers to a cDNA sequence of the target gene which can be retrieved using the GenBank accession number provided in the Target Variances by Field Table.

The third column lists the two variant sequences (SEQ ID NO:1–44) identified at the specified nucleotide. The variant nucleotides are bracketed and in bold font separated by a slash. Ten nucleotides of flanking sequence are provided on either side of the variance to localize the variant site unambiguously. (In the event of a conflict between the nucleotide number specified in column 2 and the sequence specified in column 3 the latter would rule as the correct sequence.) These variances were detected by a variety of experimental and informatics based procedures described in the examples. Many variances were detected by two independent methods (e.g. informatics based detection and T4 endonuclease VII detection).

The fourth and fifth columns (headed '# Varia 1' and '# Varia 2') provide the number of occurances of variance 1 and 2, respectively, where variance 1 is the first and variance 2 the second of the bracketed nucleotides in column three. In both the fourth and fifth columns there are two numbers. The first number reports the number of occurances of the the variance. 'Occurances' include ESTs identified during informatics based analysis, or variances identified experimentally by analysis of human cell lines, or both. The second number, inside parentheses, reports the number of individuals in whom the occurances were detected. An 'individual' means either a cell line (analyzed experimentally) or a cDNA library created from one individual (but from which many ESTs for the target gene may have been sequenced). Thus if the first number is 15 and the second number is 11 then there were 15 occurances of the variance (a combination of 15 ESTs and/or 15 experimentally identified alleles) in a total of 11 cDNA libraries and/or cell lines.

The fifth column provides annotation on the variances, particularly concerning the location of the variant site in the cDNA and the effect of the DNA sequence variance on the predicted amino acid sequence, if any. 5' UT=5' untranslated region; 3' UT=3' untranslated region; silent=variance lies in coding region by does not affect predicted amino acid sequence; ND=analysis not done; Thr->Asn=specific amino acid substitutions, inferred from the nucleotide sequence variance, are provided.

Similar information can be readily obtained for additional genes using the methods described or as known to those skilled in the art.

DETAILED DESCRIPTION OF THE PREFERRED EMBODIMENTS

As indicated in the Summary, some genes are conditionally essential, meaning that they are essential for cell survival or proliferation or provide enhanced cell survival or growth only in certain circumstances. Most commonly such circumstances are related to changes in the environment, such as changes in the concentration of specific constituents such as nutrients, administration of pharmaceuticals (drugs), or physical elements affecting the cell. In many cases the changes in the environment may be induced as part of a treatment regiment for cancer such as the administration of drugs or ionizing radiation. In the presence of such specific environmental changes or therapies, genes which are not normally essential for cell survival or proliferation become essential and, consequently, targets for therapy under the present invention. Therapy with inhibitors of conditionally essential genes involves administration of the inhibitor together with chemical or physical elements that cause the target gene to be needed for cell survival or proliferation. The use of allele specific inhibitors in the current invention allows specific killing or reduction of growth of cancer cells with such chemical or physical agents, since the gene function that is essential for the survival of cells (in the presence of the chemical or physical agent) is inhibited in the cancer cell but not in the normal cell.

The therapeutic strategy devised by the inventors can thus include: 1) identification of alternative alleles of genes coding for gene products (e.g., proteins) required or beneficial for effective cellular response to altered environmental conditions; 2) identification of the absence of one of those alleles in cancer cells; and 3a) if one of the alleles is less effective in responding to a specific altered environment, and that allele is the sole allele retained in cancer cells, then imposition of the specific altered environmental conditions to which the cancer cells are selectively less able to adapt and survive creates a differential effect on cancer cells and normal cells, or 3b) if the alleles are similar in their response to the altered environment then development of specific inhibitors of the single allele retained by cancer cells after LOH combined with imposition of the specific altered environment. The allele specific inhibitor will selectively impair the ability of the cancer cells to adapt and survive in th altered environment.

In the case of 3a), for patients with an appropriate genotype (heterozygous normal somatic cells with an active allele and a less active allele, homozygous cancer cells for the less active allele), simple imposition of the particular altered environmental conditions (e.g., physically or chemically altered) results in reduced survival or growth of the cancer cells. An extreme case of this mode occurs in patients heterozygous for a null allele and a functional allele of a conditionally essential gene which is required for adaptation of the cell to the altered conditions. In such a patient, when LOH results in loss of the functional allele in cancer cells, then treatment with the appropriate environmental alteration (e.g., a drug or radiation) will result in selective tixicity for the tumor cells. In the case of 3b), where the patient is heterozygous for two allels of comparable activity to survival or growth in the altered environment, then allele specific inhibitors can be used to prevent effective response of the cancer cells to the altered environment in situations where the cancer cells have undergone LOH and have lost an allele not targeted by the inhibitor but retain an allele which is targeted by the inhibitor. In contrast, normal cells exposed to the inhbitor are spared from the toxic effects of the inhibitor because the activity of the unblocked alternative allele is adequate to permit adaptive response to the altered environment. This differential effect of the inhibitor on cancer cells and normal cells in the presence of the altered environment can produce a high therapeutic index for such inhibitors when used as antineoplastic agents.

Thus a strategy begins with the identification of heterozygous alleles of genes coding for proteins that are conditionally essential for cell viability or growth due to change in the chemical or physical environment. In one aspect of this invention, the gene targets of this application are responsible for mediating cell response to changes in the environment. Such environmental alterations include, for example, changes in the concentration of naturally occurring constituents such as amino acids, sugars, lipids and inorganic and organic ions, as well as larger molecules such as hormones or antibodies, or changes in the partial pressure of oxygen or other gasses. The absence of a specific constituent in the environment makes the genes that are involved in synthesizing that nutrient within the cell essential, whereas if the constituent were present in the environment in sufficient quantities, such genes would not be essential. Alternatively, high concentrations of a specific constituent in the environment may make genes that are responsible for eliminating or detoxifying that constituent within the cell essential, wheras, if the constituent were absent or present in normal concentrations, such genes would not be essential. Changes thus may involve either an increase or a decrease in specific constituents of the environments including nutrients, inorganic, or organic materials.

In another aspect of this invention, the gene targets of this application are responsible for maintaining cell survival or proliferation in the presence of a drug or biological material. For example, a drug that inhibits one pathway for maintaining the level of a cellular constituent within levels required for cell survival or proliferation may make alternative pathways essential. In a specific embodiment, the inhibition of a synthetic pathway for a cellular constituent may make alternative synthetic pathways essential for cell survival or proliferation. Alternatively, a drug that is toxic to the cell will make genes that are involved in the elimination, degradation, or excretion of the drug from the cell essential for continued survival or proliferation. It will be evident to those skilled in the art that anything which inhibits the ability of a cell to survive in the presence of a specific drug that is designed to be cytostatic or cytotoxic, will sensitize that cell to the effects of the drug. A "chemosensitizing" agent is thus one that inhibits a function in the cell that is conditionally essential due to the administration of a chemotherapeutic drug.

In another aspect of this invention, the gene targets of this application are responsible for maintaining cell survival or proliferation in response to external physical forces including, but not limited to, electromagnetic radiation of various amplitudes and wavelengths, including ionizing and nonionizing radiation and heating or cooling. In the presence of ionizing radiation, for example, genes that are involved in DNA repair may be essential that are not essential in the absence of the external physical force. An agent that inhibits functions in the cell that are essential due to the adminitration of ionizing radition would be termed a "radiosensitizing" agent.

In each instance, treatment of cancer or noncancer proliferative diseases may be achieved by identifying genes that are conditionally essential in the presence of specific environmental, pharmacological, or physical factors, determining whether such genes are subject to loss of heterozygosity, identifying alternative alleles in these genes and developing allele specific inhibitors of alternative forms of the gene. The administration of such an inhibitor to a patient who has two alternative forms of the gene in normal cells but only one in the cancer cell due to LOH, together with the environmental, pharmacological or physical factors will result in an antiproliferative effect or killing of the cancer cell.

Different environmental, pharmacological, and physical changes in the environment that result in homeostatic or compensatory responses in which genes that are not normally essential for cell survival or proliferation become essential are known in the art. These are described in the following Table 1.

Table 1

1. Changes in the concentration of constituent in the environment
   Change in nutritional environment
   Change in hormonal environment
   Change in the immunological environment
   Presence or accumulation of toxic materials
   Change in partial pressure of oxygen
   Change in partial pressure of carbon dioxide.
   Change in partial pressure of other gasses including nitrous oxide
2. Administration of pharmaceuticals including small molecules, biologicals, nucleic acids, or antibodies.
3. Physical changes
   Electromagnetic radiation
   Ionizing radiation including Alpha particles, Beta particles, Gamma radiation
   Non-ionizing radiation including infrared radiation, microwave radiation, other wavelengths
   Temperature When LOH results in a difference in normal cell genotype vs. cancer cell genotype that affects a locus encoding a product affecting the cells' ability to survive in the presence of an environmental change, or a pharmaceutical or biological agent, or a physical factor, there is an opportunity to exploit a therapeutic window between cancer cells and normal cells. Below we describe specific examples of genes that (1) affect cell responses to altered environments, (2) are located on chromosomes that undergo LOH in cancer and (3) exist in two or more variant forms. These examples have been selected to illustrate how the therapeutic strategy described in this application would work with a variety of different alterations in chemical or physical environment. Example 1 describes a gene (Dihydropyrimidine Dehydrogenase) that mediates response to an altered chemical environment (presence of the toxic chemical 5-floxuridine) by specifically transforming the chemical to an inactive metabolite. Example 39 describes a gene (Methylguanine methyltransferase) that mediates response to an altered chemical environment (presence of toxic chemicals such as nitrosourea or other alkylating agents) by removing methyl or alkyl adducts to DNA, the principal toxic lesion of these agents. Example 2 describes a set of genes (Fanconi Anemia genes A,B,C,D,E,F,G and H) which mediate response to an altered chemical environment (presence of chemicals which cause DNA crosslinking, such as diepoxybutane, mitomycin C and cisplatinum) by repairing the crosslinks. Example 6 describes a set of genes (the DNA Dependent Protein Kinase Complex, including the DNA Dependent Protein Kinase catalytic subunit (DNA-PKcs), the DNA binding component (called Ku), made up of Ku-70 and Ku-86 kDa subunits, and the Ku-86 related protein Karp-1) that mediates repair of double stranded DNA breaks, such as occurs after x-irradiation. Example 3 describes a gene (asparagine synthase) that mediates response to an altered nutritional environment (absence of extracellular asparagine) which can be produced by an enzyme such as asparaginase, which hydrolyzes serum asparagine. Example 7 describes the Ataxia Telangiectasia gene, which is involved in response to ionizing radiation and radiomimetic chemicals. Other detailed examples include methionine synthase (Ex. 4) and methylthioadenosine phosphorylase (Ex. 5). Other examples include Poly (ADP) Ribose Polymerase (PARP), Glutathione-S-Transferase pi (GST-pi), NF-kappa B, Abl Kinase, 3-alkaylguanine alkyltransferase, N-methylpurine DNA glycosylase (hydrolyzes the deoxyribose N-glycosidic bond to excise 3-methyladenine and 7-methylguanine from alkylating agent-damaged DNA polymers), OGG-1, MDR-1.

The table below presents exemplary categories and exemplary specific genes along with the type of conditions which render the gene essential.

TABLE 2

Categories of Conditionally Essential Genes

Genes and Proteins Vital for Cell Survival or
Proliferation in the Presence of an Altered
Chemical or Physical Environment I. Genes Required for Adaptation to Changes in the Chemical Environment
   1. Adaptation to altered concentration of a naturally occuring small molecule
      A. Increased concentration of a naturally occuring small molecule
         i. Increased levels of amino acids
            1. Targets: amino acid degradation pathways
               Increased intracellular levels of amino acids can damage cells. One cause of such increased levels is failure to properly degrade amino acids into simpler compounds. Therefore an amino acid canalizing enzyme can be a conditionally essential gene, particularly in the presence of elevated levels of the twenty amino acids commonly used in protein synthesis. Amino acid catabolic pathways are well described in textbooks and in the scientific literature.

ib. Increased levels of sugars or starches
  2. Targets: mono, di and polysaccharide metabolic pathways
    Galactose-1-phosphate uridyltransferase
    Galactose kinase
    UDPgalactose4-epimerase
      Increased intracellular levels of sugars or starches can damage cells. One cause of increased levels is failure to properly degrade starches into simple compounds, as exemplified by diseases of impaired polysaccharide metabolism. Therefore a polysaccharide catabolizing enzyme can be a conditionally essential gene, specifically in the presence of elevated levels of particular polysaccharides. A second mechanism of damage arises in the context of impaired sugar metabolism. Thus enzymes that degrade sugars or starches to simpler compounds may be conditionally essential for cell health and consequently cell proliferation. An example is the enzymes of the Leloir pathway of galactose metabolism. Mutant copies of these proteins make cells conditionally sensitive to elevated concentrations of galactose. Thus enzymes that degrade sugars or starches to simpler compounds may be conditionally essential for cell proliferation.
iii. Increased levels of vitamins
B. Decreased concentration of a naturally occuring small molecule
  i. Decreased levels of amino acids
    1. Targets: amino acid transporters
      Decreased intracellular levels of amino acids can impair protein synthesis and thereby slow or arrest cell division. One cause of such decreased levels is impairment of cellular uptake of amino acids, particularly amino acids that the cell is not actively synthesizing, whether essential (e.g. methionine) or nonessential (e.g. asparagine; see examples). Cells have a variety of mechanisms for amino acid uptake, including membrane anchored transporters. In the presence of decreased extracellular levels of amino acids the protein and other constituents of these transporters become conditionally more essential.
    2. Targets: amino acid biosynthetic machinery
      a. Essential amino acids
        Methionine Synthase, essential for responding to decreased extracellular methionine. (GenBank U73338)
      b. Non-essential amino acid biosynthesis
        Asparagine Synthase, essential for responding to decreased extracellular asparagine. (GenBank M27396)
        Glutamine Synthase, essential for responding to decreased extracellular glutamine. (GenBank Y00387)
        Decreased intracellular levels of amino acids can impair protein synthesis and thereby slow or arrest cell division. One cause of such decreased levels is impairment of amino acid biosynthesis, particularly amino acids that the cell is not actively synthesizing, whether essential (e.g. methionine) or nonessential (e.g. asparagine; see examples). Cells have a variety of well described biochemical pathways for biosynthesis of the 20 amino acids commonly used in proteins. These biosynthetic enzymes can be conditionally essential in the absence of adequate intracellular levels of amino acids. Specific examples of such conditionally essential genes are described in the Examples. However, other enzymes which catalyze reactions important for maintaining levels of amino acids adequate for protein synthesis in the presence of decreased extracellular concentrations are also useful.
    3. Targets: transaminases
      In the presence of decreased extracellular levels of amino acids cells must increase intracellular mechanisms for amino acid biosynthesis. One such mechanism is transfer of amino groups from nonessential to essential amino acids to compensate for insufficient quantities of essential amino acids. These reactions are catalyzed by transaminases, which therefore can become conditionally essential in environments characterized by decreased levels of extracellular amino acids.
  ii. Decreased levels of sugars
    1. Targets: sugar transporters
    2. Targets: sugar metabolism machinery
      Increased intracellular levels of sugars or starches can damage cells.
    One cause of such increased levels is failure to properly degrade starches into simple compounds, as exemplified by diseases of impaired polysaccharide metabolism. Therefore a sugar or polysaccharide catabolizing enzyme can be a conditionally essential gene in the presence of elevated levels of particular sugars or polysaccharides.
2. Adaptation to presence of non-naturally occuring molecules
  A. Elimination of non-naturally occuring molecules
    i. Elimination by export
      Multidrug resistance gene/P glycoprotein (MDR1) (GenBank AF016535)
      Multidrug resistance associated proteins 1–5 (MRPs) (GenBank L05628)
        Cells have evolved specific mechanisms to export a variety of chemicals; including nonnatural chemicals such as cytotoxic drugs. MDR1 and MRP are exemplary ATP-dependent transmembrane drug-exporting pumps. Deficiency of these pumps is associated with increased sensitivity to a variety of cytotoxic drugs in vitro and in vivo. For example, mice lacking functional MRP are hypersensitive to the drug etoposide. Thus these pumps are important for cell survival in the presence of a variety of toxic drugs. Polymorphisms have been reported in MDR1 at amino acids 893 and 999. MDR also maps to a region of chromosome 7 which is frequently affected by LOH in prostate, ovarian breast and other cancers.
      Multispecific organic anion transporters (MOATs)
      Other drug export proteins
    ii. Elimination by metabolic transformation
      1. Specific metabolic transformation of drugs
        a. Inactivation of bleomycin
          Bleomycin hydrolase (GenBank U14426)
          Bleomycin hydrolase was discovered through its abililty to detoxify the anticancer glycopeptide bleomycin. Cells lacking bleomycin hydrolase are highly susceptible to bleomycin toxicty (for example pulmonary fibrosis) thus the gene is conditionally essential for cell growth and survival in the presence of bleomycin. Bleomycin hydrolase is a member of the cysteine protease papain superfamily. The protein is expresed in all tissues surveyed. The crystal structure of the closely related yeast bleomycin hydrolase has been determined. A common A/G polymorphism has been described at nucleotide 1450 of the bleomycin hydrolase gene. It results in an isoleucine-valine variance at amino acid 443, part of the oligomerization domain of the homotetrameric enzyme. The Bleomycin hydrolase gene has been mapped to the proximal long arm of chromsome 17 (17q11.2), a site of frequent LOH in commonly occuring epithelial cancers such as breast and ovarian cancer.

b. Inactivation of pyrimidine analogs including 5-fluorouracil (5-FU) and 5-fluorouridine.
Dihydropyrimidine Dehydrogenase (DPD)
β__-ureidopropionase
β-alanine synthetase
DPD is described in the examples. The other two enzymes are responsible for the further metabolism of dihydro-5-fluorouracil, the metabolic product of DPD. In the absense of these enzymes toxic metabolites of 5-FU accumulate in cells.

c. Inactivation of of pyrimidine analogs including cytosine arabinoside and 5-azacytidine.
Cytidine deaminase
Cytidine deaminase (CDA) catalyzes hydrolytic deamination of cytidine or deoxycytidine. It can also deaminate cytotoxic cytosine nucleotide analogs such as cytosine arabinoside, rendering them nontoxic. Resistance to the cytotoxic effects of these drugs has been reported associated with increased expression of the CDA gene. Thus CDA is a conditionally essential gene in the presence of cytotoxic cytosine nucleotide analogs.

d. Inactivation of thiopurine drugs, including 6-mercaptopurine, 6-thioguanine and azathioprine.
Thiopurinemethyltransferase (GenBankU12387)

e. Inactivation or transformation of other drugs including, but not limited to, purine analogs, folate analogs, topoisomerase inhibitors and tubulin acting drugs via specific enzymatic modification.

2. General metabolic transformation of drugs
a. Cytochrome P450 system.
CYP1
  CYP1A1 (GenBan K03191)
  CYP1A2 (GenBank M55053)
CYP2
  CYP2A6 (GenBank U33317)
  CYP2A7
  CYP2B6
  CYP2B7
  CYP2C8
  CYP2C9 (OMIM601130)
  CYP2C17
  CYP2C18
  CYP2C19 (OMIM 124020)
  CYP2D6 (OMIM 124030)
  CYP2E1 (OMIM 124040)
  CYP2F1
CYP3
  CYP3A3
  CYP3A4 (GenBank D00003)
  CYP3A5
  CYP3A7
CYP4
  CYP4B1
CYP7
CYPI11
CYP17
CYP19
CYP21
CYP27

The cytochrome P450s are a large gene family whose members metabolically transform and inactivate a wide variety of drugs, including cytotoxic drugs. Wide variation in P450 protein expression has been described, including null alleles. For example cytochrome P450 2D6 may be involved in the metabolism of ~25% of all drugs. Between 5 and 10% of all caucasians are homozygous for completely inactive alleles of P450 2D6. In the presence of a toxic drug the P450 enzyme responsible for metabolizing the drug may be conditionally essential. For example, acute liver faillure has been reported in a patient treated with cyclophosphamide who was homozygous for the deficient CYP 2D6B allele. Liver failure was due to accumulations of a hepatotoxic 4-hydroxylated cyclophosphamide metabolite.

b. N-acetyltransferases
c. Glucuronyltransferases
d. Glutathione transferases
  Glutathione transferase alpha (GenBank AF020919)
  Glutathione transferase theta (OMIM 600436 & 600437)
  Glutathione transferase mu (OMIM 138350, 138380, 138380, 138333 & 138385)
  Glutathione transferase pi (GenBank X65032)
  A large number of drugs are are biotransformed into electrophilic intermediary compounds which are potentially harmful to cell constituents unless rendered harmless by conjugation with glutathione. Thus proteins of the GST system are conditionally essential for cell survival.

B. Repair or prevention of damage by non-naturally occuring molecules
  i. Repair or prevention of damage by molecules that react with nucleic acids
    1. Molecules that add alkyl or other groups to DNA
      a. Targets: genes & gene products involved in repair of alkylating agent damage
        Methylguanine Methyltransferase (MGMT) (GenBank M29971)
        3-alkylguanine alkyltransferase
        3-methyladenine DNA glycosylase (GenBank M74905)
        MGMT is described in the examples. hOGG1 is a DNA glycosylase with associated lyase activity that excises this adduct and introduces a strand break. Cells lacking this protein are deficient in repair of oxidative damage and have high mutation rates. In conditions of high oxidative damage, including cellular aerobic metabolism, ionizing radiation and some chemotherapy drugs the hOGG1 gene would be conditionally essential for DNA repair. The human OGG1 gene maps to chromosome 3p25, a region of high frequency LOH in lung, kidney, head and neck and other cancers. Homozygous mutant mouse cells lacking 3-methyladenine DNA glycosylase have increased sensitivity to alkylation induced chromosome damage and cell killing.

2. Molecules that induce single or double stranded DNA breaks (also relevant to survival in the presence of ionizing radiation; see below)
 a. Targets: genes & gene products involved in repair of double stranded DNA breaks
  DNA Dependent Protein Kinase (DNA-PK) and subunits
  Catalytic subunit of DNA-PK (GenBank U47077)
  DNA binding subunit of DNA-PK (Ku subunit)
   Ku-70 subunit (GenBank J0461 1)
   Ku-86 subunit (OMIM 194364/GenBank AF039597)
  KARP-1
  Poly (ADP-ribose) polymerase (PARP) (GenBank M32721)
 b. Targets: genes & gene products that repair DNA cross-links induced by molecules such as Mitomycin C or diepoxybutane
  Fanconi Anemia genes
   Fanconi Anemia A gene (GenBank X99226)
   Fanconi Anemia B gene
   Fanconi Anemia C gene (GenBank X66894)
   Fanconi Anemia D gene
   Fanconi Anemia E gene
   Fanconi Anemia F gene
   Fanconi Anemia G gene
   Fanconi Anemia H gene
4. Targets: genes & gene products required for repair of DNA damage caused by drugs such as, for example, 4-nitroquinoline-1-oxide, bromobenz(a)anthracene, benz(a)anthracene epoxide, 1-nitorpyridine-1-oxide, acetylaminofluorine and aromatic amides, benz(a)pyrene.
 a. Nucleotide excision repair system
  ERCC-1 (GenBank M13194)
  ERCC2/XPD (GenBank X52222)
  ERCC3/XPB (GenBank M31899)
  ERCC4 (OMIM 133520)
  ERCC5 (GenBank L20046)
  ERCC6 (GenBank L04791)
 b. Other DNA repair genes
  XPA (GenBank D14533)
  XPC (GenBank D21090)
  XPE (GenBank U18300)
  HHR23A (GenBank U21235)
  HHR23B (GenBank D21090)
  Uracil glycosylase (GenBank X52486)
  3-methyladenine DNA glycosylase (GenBank M74905)
ii. Repair of damage by chemicals that interact with proteins
iii. Repair of damage by chemicals that interact with membranes
1. Free radical damage iv. Adaptation to molecules that alter the cellular redox state (such as pyrrolidinedithiocarbamate)
3. Adaptation to change in nutritional environment
 A. Decreased levels of nutrients.
 B. Increased levels of nutrients.
4. Change in hormonal environment
 A. Decreased levels of hormones.
 B. Increased levels of hormones.
5. Change in the immunological environment
 A. Introduction of new immune molecules (antibodies or antibody fragments)
 B. Introduction of immune regulatory molecules
  Fanconi anemia C
  NF-kappa B (GenBank M58603)
   Cells lacking the Fanconi anemia C gene have been shown hypersensitive to interferon gamma in vitro. Cells lacking the RelA/p65 subunit of NF kappa B are essential for preventing Tumor Necrosis Factor alpha induced cell death. Other Fanconi anemia genes or other proteins of the NF-Kappa B system and its regulators, for example I kappa B, may also mediate sensitivity to immune system molecules, for example interferons, interleukins or TNF.
II. Changes in physical environment
 1. Repair of damage caused by electromagnetic radiation
  A. Repair of damage caused by ionizing radiation (Alpha particles, Beta particles, Gamma radiation)
   i. DNA-PK constitutents (see above)
   ii. Other proteins that repair DNA damage created by DNA-PK
    XRCC4 (GenBank U40622)
    XRCC5/Ku8O (OMIM 194364)
    XRCC6
    XRCC7 (GenBank L27425)
   iii. Other proteins that repair or protect from DNA damage
    Glutathione-S-transferase (alpha, theta, mu and pi proteins)
     Transfection of an exogenous Glutathione-S-transferase pi (GST-pi) gene is partially protective of cells treated with ionizing radiation. Thus GST activity is conditionally essential for cells exposed to ionizing radiation. Similarly, any protein that is essential for the repair of radiation induced damage or for protection of cells from radiation induced damage is a conditionally essential gene. GST activity can also affect radiation sensitivity in the presence of electron affinic drugs such as the nitroimidazoles.
    I-kappa B alpha (GenBank M69043)
     Increased expression of exogenous I kappa B-alpha, an inhibitor of NF-kappa B, increases cell sensitivity to ionizing radiation. Thus is conditionally essential for cells exposed to ionizing radiation. Other proteins of the NF kappa B pathway that affect radiosensitivity are likewise conditionally essential in the presence of ionizing radiation.
  B. Non-ionizing radiation
   i. infrared radiation
   ii. ultra high frequency electromagnetic radiation (UBF)
    Glutathione S transferase system (see genes listed above)

UHF electromagnetic radiation of 434 Mhz will change resonance of the glutathione cycle resulting in thiol depletion which increases radiosensivity. UHF is therefore a radiosensitizing treatment, contingent on the status of the glutathione system.

iii. Other wavelenths of electromagnetic radiation

2. Temperature

A. Heating

1. Heat shock proteins

HSP70 (OMIM 138120)

HSP27 (GenBank X54079)

B. Cooling

2. Cold sensitive proteins

3. Change in redox environment, including change in partial pressure of gasses

A. Change in partial pressure of oxygen i. Repair of damage from reactive oxygen species 8-oxoguanine DNA glycosylase (hOGG1) (GenBank U96710)

The major mutagenic lesion caused by exposure to reactive oxygen species is 8-oxogunine. hOGG1 is a DNA glycosylase with associated lyase activity that excises this adduct and introduces a strand break. Cells lacking this protein are deficient in repair of oxidative damage and have high mutation rates. In conditions of high oxidative damage, including cellular aerobic metabolism, ionizing radiation and some chemotherapy drugs the hOGG1 gene would be conditionally essential for DNA repair. The human OGG1 gene maps to chromosome 3p25, a region of high frequency LOH in lung, kidney, head and neck and other cancers.

Fanconi anemia genes (see above for list of 8 FA complementation groups; FA genes also mediate sensitivity to oxygen)

B. Change in partial pressure of carbon dioxide.

C. Change in partial pressure of other gases.

In addition to being hypersensitive to ionizing radiation Ataxia-Telangiectasia cells are hypersensitive to the nitric oxide donor S-nitrosoglutathione (GSNO), as are cells from some radiosensitive individuals without ataxia. GSNO induces dose-dependent DNA strand brekage; cell killing appears to be associated with formation of nitrite as the ultimate oxidation product of nitric oxide. Any protein important for response to damage induced by a dissolved gas is a conditionally essential gene in this category.

II. Identification of variances and alternative alleles.

A target gene of this invention occurs as alternative alleles in a population; that is, the DNA sequence variance should either affect the gene sequence, RNA sequence, or protein sequence of the gene or its gene products, which would facilitate the design of inhibitors of the protein product, or be a base difference anywhere within the genomic DNA sequence, including the promoter or intron regions. Such DNA sequence variance can be exploited to design inhibitors of transcription or translation which distinguish between two allelic forms of the targeted gene. Sequence variants that do not alter protein sequence can be targeted, for example, with antisense oligonucleotides or ribozymes.

The most elementary genetic variant, which is common in mammalian genomes, is the single nucleotide substitution. It has been estimated that the comparison of haploid genomes will reveal this type of variant every 300 to 500 nucleotides (Cooper, et al., *Human Genetics*, 69:201:205 (1985)).

Sequence variances are identified by testing DNA from multiple individuals from the population(s) to determine whether the DNA sequence for the target gene differs in different individuals. Many different methods for identifying gene sequence variances are known in the art and can be utilized in connection with potential target genes. These include, but are not limited to: (1) sequencing using methods such as Sanger sequencing which is commonly performed using automated methods; (2) Single Strand Conformation Polymorphism (SSCP); (3) denaturing gradient gene electrophoresis (DGGE); (4) Computational methods utilizing sequence comparisons from multiple entries in sequence databases; (5) Chemical cleavage, (6) HPLC; (7) Enzymatic Mutation Detection methods; (8) Hybridization; (9) Hybridization arrays; and (10) Mass spectroscopy. Several of these methods are described in Housman et al., TARGET GENES FO RALLELE-SPECIFIC DRUGS, supra.

Often combinations of these methods are used, and are partiuclarly useful for confirmation of putative variances. For example, methods such as SSCP, DGGE, or HPLC are useful in identifying whether amplified gene segments from two individuals are identical or contain a variance. These methods do not identify the location of the variant site within the linear sequence of the amplified gene segment, nor do these methods identify the specific nature of the variance, namely the alternative bases within the variant site. Methods such as Enzymatic Mutation Detection determines where the variant site is located within the sequence, but not the specific variance. Methods such as mass spectroscopy identify the specific variance, but not its location within the segment. Methods such as sequencing, computational analysis, and hybridization arrays can determine the location of the variance and specific sequence of the variance within the segment. In addition, methods such as SSCP, DGGE, EMD, and chemical cleavage are useful for determining alleles containing more than one variant site, if such sites occur within a single amplified gene segment. For the purpose of this invention, such methods have been used to identify variant sites within genes that are conditionally essential. With the above methods, the presence and type of variance are preferably confirmed, such as by sequencing PCR amplification products extending through the identified variance site.

III. Loss of Hertozygosity

Genes which are located in chromosomal regions which frequently undergo LOH in a tumor or other disease or condition provide advantageous targets, as the LOH of the chromosomal region indicates that the particular gene will also undergo LOH at similar high frequency. Also, genes which undergo LOH at high frequencies in a particular tumor, or in a range of tumor types provide advantageous targets, as a large number of patients will be potentially treatable due to the LOH of a particular essential gene.

Cancer cells, or more broadly, cells associated with certain other proliferative conditions, are generally genetically different from normal somatic cells as a result of partial or complete chromosome loss, called loss of heterozygosity (LOH), which occurs at the earliest stages of these disorders. In cancer, as a result of such early chromosome loss, all the tumor cells in an individual exhibit the same pattern of LOH since the cancer results from clonal expansion of the progenitor cell with LOH. Losses of genes in LOH range from less than 5% of a chromosome, to loss of a chromosome arm, to loss of an entire chromosome. Generally only one chromosome copy is lost, making cancer cells partially hemizygous—i.e., they have only one allele of many genes. As a result of such allele loss, only the single remaining allele will be available to be expressed. Such loss of heterozygosity and other losses of genetic material in cancers is described in a variety of references, for example in Mitelman, F., *Catalog of Chromosome Aberrations in Cancer*, New York: Liss (1988); and Seizinger, et al., "Report of the committee on chromosome and gene loss in neoplasia," *Cytogenet. Cell Genetics*, 58:1080–1096 (1991). A review of many published studies of LOH in cancer cells is provided in Lasko, Cavenee, and Nordenskjold, "Loss of Constitutional Heterozygosity in Human Cancer," *Ann. Rev. Genetics*, 25:281–314 (1991).

There is considered to be a causal relationship between LOH and the origin of cancer or other proliferative disorders. Loss of heterozygosity commonly involves chromosomes and chromosome segment that contain at least one tumor suppressor gene in addition to many other genes that may not have any finction associated with cancer but are coincidentally located in the same region of the chromosome, measured in physical distance or genetic distance, as the tumor suppressor gene. Tumor suppressor genes generally regulate cell proliferation or are involved in initiating programmed cell death when threshold level of damage occurs to the cell. The loss of tumor suppressor gene function is believed to confer a growth advantage to cells undergoing LOH, because it allows them to evade these negative growth regulatory events. It is the loss of tumor suppressor genes, and the proliferative advantage associated with loss of tumor suppressor functions, that drives allele loss or loss of heterozygosity. Loss of tumor suppressor gene function requires inactivation of both gene copies. Inactivation is usually due to the presence of mutations on one gene copy and partial or complete loss of the chromosome, or chromosome region, containing the other gene copy. (Lasko et al., 1991, *Annu. Rev. Genet.* 25:281–314)

Several tumor suppressor genes have been cloned. They include, for example, TP53 on chromosome arm 17p, BRCA1 on 17q, RB and BRCA2 on 13q, APC on 5q, DCC on 18q, VHL on 3p, and p16$^{INK4}$/MTS1 on 9p. Many other, as yet uncloned, tumor suppressor genes are believed to exist based on LOH data; research groups are currently working to identify new tumor suppressor genes at more than a dozen genomic regions characterized by high LOH in cancer cells, including generating detailed LOH maps which provide LOH information useful for this invention due to the ability to identify essential genes which map to these regions of LOH. While there is an extensive literature considering tumor suppressor genes as potential targets for anti-cancer therapy, these genes are, in general, not candidates for antiproliferative therapy under the present invention because most tumor suppressor genes are not essential for cell proliferation or survival. It is the loss of tumor suppressor genes that enables the abnormal proliferation and survival of cancer cells.

The pattern of LOH for a particular cancer or tumor or other proliferative disorder is not merely random. Often, there is a characteristic pattern for each major cancer type. Certain regions, including segments of chromosomes 3, 9, 11, 13, and 17, are frequently lost in most major cancer types. Other regions, such as on chromosomes 1, 3, 5, 6, 7, 8, 9, 11, 13, 16, 17, 18, and 22, exhibit high frequency LOH in selected cancers. It is believed that the characteristic LOH patterns of different cancers reflects the location(s) of tumor suppressor genes related to the development of the particular cancer or cancer type. Thus, essential genes located in regions which are characteristically associated with LOH for a particular cancer, or other tumor are particularly advantageous targets for inhibitors useful for treatment of that cancer or tumor because such genes will also characteristically undergo LOH at high frequency. Useful parameter for describing high frequency LOH chromosomal regions are described in Housman et al., TARGET GENES FOR ALLEL-SPECIFIC DRUGS, supra.

IV. Characteristics of allele-specific inhibitors

As indicated above "allele specific inhibitors" or "allele specific anti-neoplastic agents" represent a new approach to tumor therapy because they are lethal or significantly inhibit the growth only of tumor cells. The advantages of this approach include, first, lack of toxicity to the normal cells of the patient resulting in a therapeutic index greater than that of conventional tumor, e.g., cancer chemotherapy drugs, and second, it is not necessary that the inhibitors be targeted specifically to the tumor cells, as they can be administered systemically. As also described above, usually an allele specific inhibitor is specific for a single sequence variance of a target gene, though in some cases the inhibitor utilizes the joint effects of two or more sequence variances on a particular allele. It is not necessary for the allele specific inhibitor to have absolute specificity. Normal cells expressing equal amounts of two allelic forms of a gene product encoded by the target gene will often show a reduction in survival or growth under the altered conditions when they take up the inhibitors of this invention, but should remain viable due to the activity of the protein encoded by the uninhibited allele. On the other hand, tumor cells expressing only one allele due to LOH, will respond to the inhibitors of this invention which are specifically directed to the remaining allele, with a greater reduction in viability under the altered conditions. Growth of tumor cells exposed to the inhibitors of this invention will be inhibited due to the suppression of either the synthesis or the biological activity of the target gene product.

Also, while a single gene has only two allelic forms in any given individual, the gene can have more than two allelic forms in a human population. Accordingly, inhibitors can be targeted to any of the alleles in the population. A particular inhibitor will generally be targeted to a subset of the allelic forms; the members of the subset will have a particular sequence variance which provides the specific targeting. In some cases, however, the inhibitor will jointly target two, or possibly more sequence variances.

Once two or more alleles are identified for a target gene, inhibitors of high specificity for an allele can be designed or identified empirically. Inhibitors that can be used in the present invention will depend on whether allelic variation at a target locus affects the amino acid sequence, the mRNA sequence, or the DNA in intron and promoter regions. If there is variation at the protein level, then classes of inhibitors would include low molecular weight drugs, oligopeptides and their derivatives, and antibodies, including modified or partial antibody fragments or derivatives. For mRNA or DNA sequence variances, the main class of inhibitors are complementary oligonucleotides and their derivatives and catalytic RNA molecules such as ribozymes and DNAzymes, including modified ribozymes. The generation of inhibitors of this invention can be accomplished by a number of methods. The preferred method for the generation of specific inhibitors of the targeted allelic gene product uses computer modeling of both the target protein and the specific inhibitor. Other methods include screening compound libraries or microorganism broths, empirical screening of libraries of peptides displayed on bacteriophage, and various immunological approaches.

Further, in the treatment of cancer patients, a therapeutic strategy includes using more than one inhibitor of this invention to inhibit more than one target. In this manner, inhibitors directed to different proteins can be targeted and inhibited simultaneously. Particularly advantageous is the targeting of genes which are conditionally essential under the same type of conditions, such that the effects on cell growth or survival are at least partially additive.

A. Targeted Drug Design.

Computer-based molecular modeling of target proteins encoded by the various alleles can be used to predict their three-dimensional structures using computer visualization techniques. On the basis of the differences between the three-dimensional structure of the alternate allelic forms of the proteins, determinants can be identified which distinguish the allelic forms. Novel low molecular weight inhibitors or oligopeptides can then be designed for selective binding to these determinants and consequent allele-specific inhibition. Descriptions of targeted drug design can be found, for example, in I. Kuntz, "Structure-Based Strategies for Drug Design and Discovery," *Science* 257:1078–1082 (1992) and J. Dixon, "Computer-Aided Drug Design: Getting the Best Results," *Trends in Biotechnology* 10:357–363 (1992). Specific applications of the binding of molecules to receptors using computer modeling have been described in Piper et al., "Studies Aided by Molecular Graphics of Effects of Structural Modifications on the Binding of Antifolate Inhibitors to Human Dihydrofolate Reductase," *Proc Am. Assoc. Cancer Res. Annual Meeting* 33:412 (1992); Hibert et al., "Receptor 3D-Models and Drug Design," *Therapie* (Paris) 46:445451 (1991)(serotonin receptor recognition sites). Computer programs that can be used to conduct three-dimensional molecular modeling are described in G. Klopman, "Multicase 1: A Hierarchical Computer Automated Structure Evaluation Program," *Quantitive Structure-Activity Relationships*, 11:176–184 (1992); Pastor et al., "The Edisdar Programs Rational Drug Series Design," *Quantitative Structure-Activity Relationships*, 10:350–358 (1991); Bolis et al., "A Machine Learning Approach to Computer-Aided Molecular Design," *J. Computer Aided Molecular Desig*, 5:617–628 (1991); and Lawrence and Davis, "CLIX: A Search Algorithm for Finding Novel Ligands Capable of Binding Proteins of Known Three-Dimensional Structure," *Proteins Structure Functional Genetics* 12:31–41 (1992).

Low molecular weight inhibitors specific for each allelic protein form can be predicted by molecular modeling and synthesized by standard organic chemistry techniques. Computer modeling can identify oligopeptides which block the activity of the product of the target gene. Techniques for producing the identified oligopeptides are well known and can proceed by organic synthesis of oligopeptides or by genetic engineering techniques. R. Silverman, *The Organic Chemistry of Drug Design and Drug Action*, Academic Press (1992).

The inhibitors of this invention can be identified by selecting those compounds that selectively inhibit the growth of cells expressing one allelic form of a gene, but do not inhibit the activity of the A allelic form.

B. Small Molecule Inhibitors

Low molecular weight inhibitors can be identified and generated by at least one of the following methods; (1) screening of small organic molecules present in microorganism fermentation broth for allele-specific activity; or (2) screening of compound libraries. Once a compound is identified which exhibits allele specific activity, derivatives of that compound can be obtained or produced in order to obtain compounds having superior properties, such as greater activity, greater specificity, or better administration related properties (e.g., solubility, toxicity, and others).

A small molecule for allele specific targeting, i.e., variance specific targeting, to a polypeptide or protein target will generally have the following characteristics:

Differential binding affinity for protein domains altered by the amino acid variance or uniform binding to the protein with differential effects due to subsequent interactions with variant residues.

Inhibition of protein finction following differential binding. Several mechanisms of inhibition are possible including:
competitive inhibition of active sites or critical allosteric sites,
allosteric inhibition of protein function,
altering compartmentalization or stability, and
inhibition of quaternary associations.

Favorable pharmaceutical properties, such as safety, stability, and kinetics.

In view of the art relating to identification of compounds that interact with particular features of a polypeptide or protein or protein complex, there are clear precedents for developing drugs, i.e., inhibitors, that are variance-specific, including drugs that are allosteric inhibitors of protein functions. Several lines of experimental evidence demonstrate that small molecule variance specific inhibitors can be designed and constructed for particular targets. Specifically:

Several essential gene targets have been identified that contain variances within domains comprising the active site.

It is possible to screen for ligands that recognize variant surface features.

Combinatorial methods using antibodies, peptides, or nucleic acids suggest that specific ligands can be selected for large fractions of the surface of any protein.

There are many literature reports of single amino acid substitutions, within the active site as well as elsewhere within a protein, altering ligand specificity and drug action.

Allosteric (noncompetitive) inhibition of protein function may be induced by binding ligands to many different surfaces of a protein. Ligands can cause allosteric inhibition by disturbing secondary, tertiary or quaternary (subunit-subunit) interactions of a protein. There is ample evidence that such effects can e induced by binding to sequences outside the active site and even in regions that are uninvolved in the normal catalytic or regulatory activity of a protein.

Each of these points is discussed in more detail below.

Variances Located Within Domains Comprising the Active Site.

Crystal structures are available for several of the exemplary targets or for homologous proteins that can allow prediction of tertiary structure. As noted, the protein variance in Replication Protein A occurs within the domain that is involved in binding DNA. The protein variance in CARS occurs within the domain involved in tRNA binding.

The proximity of the active site to these variances may be exploited by several different strategies:

- Competitive inhibitors can exert variance-specific effects by exhibiting differential affinities for variant active sites, thereby interfering with binding of the substrate or critical allosteric effectors.
- Competitive inhibitors may bind with equal affinity for the active site but exerting different effects on the structure or function of the variant domain.
- Allosteric inhibitors can exert variance-specific effects by binding differentially to variant forms of the active domain and distorting the structure or function of the active site.

Screening for Ligands that Recognize Variant Surface Features.

Combinatorial libraries of antibodies, peptides, nucleic acids, or carbohydrates have been used to demonstrate that ligands can be identified that will bind to large fractions of the surface of any protein.

A library of $6.5 \times 10^{10}$ antibody-bearing phage was screened for binding to various targets and contained antibodies against all targets tested.

Selex and Aptamer technologies involve selection of random oligonucleotides that bind to specific targets. Reports indicate that ligands with high affinity and specificity can be selected for diverse targets despite the limited chemical diversity of the nucleic acid-based ligands.

These studies demonstrate the ability to identify ligands for unique surface features using several different chemistries. Similarly, small molecule protein surface interaction can be screened; two broad approaches for identifying small molecule ligands can be distinguished:

Combinatorial approaches coupled with methods for high-throughput screening provide a similar scope of opportunities as combinatorial methods focused on nucleic acids, peptides, or carbohydrates.

Rational design or focused combinatorial approaches based on biochemical, biophysical, and structural data about the target protein may be optimal when the crystal structure of the protein is known. When the crystal structure of the target protein or its homologues are known it will often be possible to model the topology and surface chemistry of the target in detail. These data are usefull in optimizing the binding specificity or allosteric inhibitory function of the product through a series of iterative steps once a prototype binding ligand is identified. Structural modeling of the target can be particularly useful in optimizing the variance specificity of a ligand that binds to the target sequence.

Examples of single amino acid substitutions altering sensitivity to small molecules Many amino acid substitutions have been described in proteins that alter the specificity or function of small-molecule ligands. These substitutions are useful models for variance-specific interactions (e.g. interactions that are altered by the amino acid substitutions that distinguish variant forms of a protein.)

There are clear precedents for variance-specific drug effects in humans. Variance-specific interactions are observed in a wide variety of structurally and functionally heterogeneous proteins. Among these are variances in human proteins including:

N-acetyl transferase 2—variances affect acetylation of drugs including caffeine and arylamines;

CYP2C19—variances affect the hydroxylation of mephenytoin and related compounds;

CYP2D6—variances affect hydroxylation of debrisoquine and related compounds;

glucose-6-phosphate dehydrogenase—variances account for sensitivity to primaquine and other drugs.

There are numerous examples of variance-specific drug effects in targets for antiviral and antimicrobial drugs. The most extensively characterized are those in HIV Reverse Transcriptase and β-lactamase. These data indicate that many different amino acid substitutions can alter drug effects. Moreover, while amino acid substitutions are classically distinguished as "conservative" or "non-conservative," it is evident from these data that many seemingly "conservative" substitutions can have significant effects. For each of the types of amino acid substitution identified within the exemplary target genes, examples of the same amino acid substitution altering the interaction of small molecule drugs on a target protein is shown in one or more of the model systems.

Sites of Allosteric Inhibition

Most drug development focuses on competitive inhibitors of protein action rather than noncompetitive, allosteric inhibitors. There is no a priori advantage to a competitive versus allosteric inhibitor except for the fact that medicinal chemistry often begins with candidate molecules derived from natural substrates or cofactors. There are, in fact, conceptual advantages to allosteric inhibitors since each protein may contain multiple allosteric sites, and allosteric inhibitors may be effective at lower concentrations (e.g. those equivalent to the substrate) since there is no need to compete with the substrate for binding.

Detailed crystallographic and other structural studies of a variety of enzymes show that the mechanism of allosteric inhibition commonly involves conformational changes (e.g. domain movements) far from the site of contact with the allosteric regulator. These data illustrate the cooperativity of protein structure, demonstrating how a small change in one region of a protein is amplified throughout the structure. Such cooperativity allows small molecules binding to various regions of a protein to have significant structural and functional effects.

One way to assess the probability of achieving allosteric effects from a variant sequence is to examine the distribution and nature of mutations that affect drug action in several well-characterized proteins. Another is to examine the distribution of epitopes for antibodies that bind to the surface of a protein and inhibit its function. Analyses of these types show that allosteric sites are widely dispersed within proteins and may comprise the majority of the protein's surface.

For example:

HIV-1 Reverse Transcriptase (RT) is a Heterodimer with p66 and p51 Subunits.

The p66 subunit is 560 amino acids, and p51 is a 440 amino acid subfragment of p66. The three dimensional structure of HIV-1 RT has been solved by x-ray crystallography. Three HIV-1 RT structures have been published, including complexes with double stranded DNA at 3.0 Å resolution and with the non-nucleoside inhibitors nevirapine (at 3.5 Å) and -APA (at 2.8 Å).

Two classes of HIV-1 RT inhibitors have been developed. The first class comprises nucleoside analogues including AZT, ddI and ddC. The second class comprises non-nucleoside analogues belonging to several chemical groups, including TIBO, BHAP, HEPT, -APA, dipyridodiazepinone, pyridinone, and inophyllum derivatives, all of which bind the same hydrophobic pocket in HIV RT. Many amino acid substitutions have been described that produce resistance to these drugs. It has been shown that nucleoside analog resistance arises from mutations in multiple domains. Many of the mutations are located far from the dNTP binding sites. These changes inhibit drug function by altering the conformation of the target protein in a manner analogous to those conformational changes that may be induced by an allosteric inhibitor.

Thyrotropin receptor Naturally occurring antibodies against the thyrotropin receptor can cause activation of thyroid finction (Grave's disease) or inhibition of thyroid function (Hashimoto's disease). The sites within the thyrotropin receptor that are targeted by these natural antibodies have been mapped in detail and have been tested with monoclonal antibodies. Most of the inhibitory antibodies do not interfere with binding of thyrotropin to its receptor, and thus, are allosteric rather than competitive inhibitors. Several independent classes of inhibitory antibodies have been identified that bind to epitopes within different domains of the receptor. At least one of these epitopes is in a domain that is entirely unimportant for receptor activity and can be deleted by site-directed mutagenesis without disrupting the finction of the receptor. These experiments provide an explicit precedent for achieving allosteric inhibitory effects from ligands that target widely dispersed sequences within the protein.

Thermus aquaticus DNA polymerase The inhibitory activity of 24 monoclonal antibodies to *Thermus aquaticus* DNA polymerase has been investigated. The antibodies recognized 13 non-overlapping epitopes. Antibody binding to eight epitopes was inhibitory. Inhibitory antibodies mapped to several distinct domains, including the 5' nuclease domain, the polymerase domain and the boundary region between the 5' nuclease and polymerase domains. Some antibodies recognized epitopes overlapping the DNA binding groove of the polymerase. Significantly, the inhibitory antibodies recognized epitopes constituting as much as 50% of the Taq polymerase surface, and the non-inhibitory antibodies a further ~25%.

β-lactamase The β-lactamases are a diverse family of enzymes which catalyze the hydrolysis of the β-lactam ring of penicillin and cephalosporin antibiotics. Interactions of these proteins with various small molecule drugs have been characterized in detail as the pharmaceutical industry has worked to develop chemically modified penicillins and cephalosporins to elude inactivation by β-lactamases. In addition, a β-lactamase inhibitor (clavulanic acid) has also been introduced into clinical use.

As each new drug has been introduced into wide use, mutant β-lactamases have emerged that are resistant to the drug. Over 190 β-lactamases have been described with differential specificity for the various penicillins and cephalosporins. Many of these differ by only a few amino acids. Many different amino acid substitutions at various sites within the protein can change the substrate specificity of the enzyme.

kat G (Isoniazid resistance) The kat G protein of *M. tuberculosis* encodes a catalase-peroxidase enzyme that is one of two mycobacterial genes frequently altered in isoniazid resistant strains (the other is inhA). There are a wide variety of amino acid substitutions in katG associated with drug resistance distributed evenly across the 740 amino acids of the protein. The mechanism by which some of these substitutions inhibit katg function can be inferred from the structure of the homologous yeast and *E. coli* enzymes and knowledge of the catalytic function of the enzyme. For example, insertion of an Ile between positions 125 and 126 affects a conserved interhelical loop near the active site residues; substitutions at amino acid 275 and 315 are likely to affect the ligand access channel; substitutions at amino acid 463 may affect a N-terminal substrate binding site. Other substitutions occur in regions that are not directly related to the functional sites of the protein.

The examples described above demonstrate that small molecules can discriminate in activity between polypeptides or proteins which have one a single amino acid difference in sequence, i.e., a single amino acid sequence variance.

C. Antibody Inhibition.

Once a potential target gene is identified and is determined to exist in two or more allelic forms which encode different proteins, antibodies can be raised against both (or more) allelic forms of the protein. The techniques for using a specific protein or an oligopeptide as an antigen to elicit antibodies which specifically recognize epitopes on the peptide or protein are well known. Preferably monoclonal antibodies (MABs) are used.

In one embodiment, the DNA sequence of the desired allelic form of the target gene can be cloned by insertion into an appropriate expression vector and translated into protein in a prokaryotic or eukaryotic host cell. The protein can be recovered and used as an antigen to elicit the production of specific antibodies. In another embodiment, the DNA of the desired allelic form of the target gene is amplified by PCR technology and is subsequently translated in vitro into protein to be used as the antigen to elicit the production of specific antibodies. A third embodiment is to use the DNA sequence of the alternative alleles as a basis for the generation of synthetic peptides representing the amino acid sequence of the alleles for use as antigen to elicit the production of specific antibodies.

Antibodies can be generated either by standard monoclonal antibody techniques or generated through recombinant based expression systems. See generally, Abbas, Lichtman, and Pober, *Cellular and Molecular Immunology*, W. B. Saunders Co. (1991). The term "antibodies" is meant to include intact antibody molecules of the IgD isotype as well as antibody fragments or derivatives, such as Fab and F(ab')2, which are capable of specifically binding to antigen. The antibodies so produced will preferentially bind only the protein produced in the allelic form which was used as an antigen to create the antibody. If the targeted protein is expressed on the cell surface, the antibody or antibody derivative can be tested as a therapeutic. Antibody inhibitors are most effective when they are directed against cell surface proteins or receptors. If the protein produced by the targeted allele is not a cell surface protein or receptor, the development of antibody inhibitors may also require the use of a special antibody-delivery system to facilitate entry of the antibody into the tumor cells. The plasma membrane that surrounds all cells is designed to limit the entrance of most compounds. Entry is generally restricted to small, non-charged molecules (absence of charge allows them to slip through the fatty membrane) or to those factors that can penetrate the cell using existing, specialized import mechanisms. The introduction into cells of much larger molecules, such as specific antibodies, other proteins, or peptides, requires appropriate delivery systems such as are known in the art. Alternatively, the structure of the variable region of allele specific antibodies can be used as the basis for design of smaller allele specific inhibitory molecules.

D. Oligopeptides

Oligopeptides can be demonstrated to have a very high degree of specificity in their interaction with functional polypeptides such as cellular enzymes, receptors or other polypeptides essential for cell viability. Methods for screening peptide sequences which have high specificity for binding to, and functional inhibition of, a specific polypeptide target have been well described previously. Scott, J. K. and Smith G. P., "Searching for Peptide Ligands with an Epitope Library," *Science* 249:386–390 (1990). These methods include the screening of M13 libraries by "phage display" of polypeptide sequences as well as direct screening of peptides or mixtures of synthetic peptides for binding to or inhibition of the target functional polypeptide. The oligopeptides of this invention can be synthesized chemically or through an appropriate gene expression system. Synthetic peptides can include both naturally occurring amino acids and laboratory synthesized, modified amino acids.

Also provided herein are functional derivatives of a polypeptide or protein. By "functional derivative" is meant a "chemical derivative," "fragment," "variant," "chimera," or "hybrid" of the polypeptide or protein, which terms are defined below. A functional derivative retains at least a portion of the function of the protein, for example reactivity with a specific antibody, enzymatic activity or binding activity mediated through noncatalytic domains, which permits its utility in accordance with the present invention.

A "chemical derivative" of the complex contains additional chemical moieties not normally a part of the protein. Such moieties may improve the molecule's solubility, absorption, biological half life, and the like. The moieties may alternatively decrease the toxicity of the molecule, eliminate or attenuate any undesirable side effect of the molecule, and the like. Moieties capable of mediating such effects are disclosed in Remington's Pharmaceutical Sciences (1980). Procedures for coupling such moieties to a molecule are well known in the art. Covalent modifications of the protein or peptides are included within the scope of this invention. Such modifications may be introduced into the molecule by reacting targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetarnide, to give carboxymethyl or carboxyamidomethyl derivatives. Cysteinyl residues also are derivatized by reaction with bromotrifluoroacetone, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect or reversing the charge of the lysinyl residues. Other suitable reagents for derivatizing primary amine containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine alpha-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'-N-C-N-R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residue are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking component peptides to each other or the complex to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[p-azidophenyl) dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., Proteins: Structure and Molecular Properties, W. H. Freeman & Co., San Francisco, pp. 79–86 (1983)), acetylation of the Nterminal amine, and, in some instances, amidation of the C-terminal carboxyl groups.

Such derivatized moieties may improve the stability, solubility, absorption, biological half life, and the like. The moieties may alternatively eliminate or attenuate any undesirable side effect of the protein complex and the like. Moieties capable of mediating such effects are disclosed, for example, in *Remington's Pharmaceutical Sciences*, 18th ed., Mack Publishing Co., Easton, Pa. (1990).

The term "fragment" is used to indicate a polypeptide derived from the amino acid sequence of the protein or polypeptide having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence.

Another functional derivative intended to be within the scope of the present invention is a "variant" polypeptide which either lack one or more amino acids or contain additional or substituted amino acids relative to the native polypeptide. The variant may be derived from a naturally occurring polypeptide by appropriately modifying the protein DNA coding sequence to add, remove, and/or to modify codons for one or more amino acids at one or more sites of the C-terminus, N-terminus, and/or within the native sequence.

A functional derivative of a protein or polypeptide with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, *DNA* 2:183) wherein nucleotides in the DNA coding the sequence are modified such that a modified coding sequence is produced, and thereafter expressing this recombinant DNA in a prokaryotic or eukaryotic host cell, using techniques such as those described above. Alternatively, components of functional derivatives of complexes with amino acid deletions, insertions and/or substitutions may be conveniently prepared by direct chemical synthesis, using methods well-known in the art.

E. Complementary Oligonucleotides and Ribozymes

Oligonucleotides or oligonucleotide analogs which interact with complementary sequences of cellular target DNA or RNA can be synthesized and used to inhibit or control gene expression at the levels of transcription or translation. The oligonucleotides of this invention can be either oligodeoxyribonucleotides or oligoribonucleotides, or derivatives thereof, which are complementary to the allelic forms of the targeted gene or they can act enzymatically, such as ribozymes. Both antisense RNA and DNA can be used in this capacity as chemotherapeutic agents for inhibiting gene transcription or translation. Trojan, J., et al., "Treatment and prevention of rat glioblastoma by immunogenic C6 cells expressing antisense insulin-like growth factor I RNA," *Science* 259:94–97 (1993). Inhibitory complementary oligonucleotides may be used as inhibitors for cancer therapeutics because of their high specificity and lack of toxicity.

Included in the scope of the invention are oligoribonucleotides, including antisense RNA and DNA molecules and ribozymes that function to inhibit expression of an essential gene in an allele specific manner. Anti-sense RNA and DNA molecules act to directly block the translation of mRNA by binding to targeted mRNA and preventing protein translation or directing RNase mediated degradation of the mRNA. With respect to antisense DNA, oligodeoxyribonucleotides derived from the translation initiation site, e.g., between −10 and +10 regions of the relevant nucleotide sequence, are preferred.

Ribozymes are enzymatic RNA molecules capable of catalyzing the specific cleavage of RNA. The mechanism of ribozyme action involves sequence specific interaction of the ribozyme molecule to complementary target RNA, followed by a endonucleolytic cleavage. Within the scope of the invention are engineered hammerhead, hairpin, and other motif ribozyme molecules that catalyze sequence specific endonucleolytic cleavage of RNA sequences encoding a gene product essential for cell survival, growth, or vitality.

Specific ribozyme cleavage sites within any potential RNA target can initially be identified by scanning the target molecule for ribozyme cleavage sites, such as sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays. See, for example, Draper PCT WO 93/23569. For the present invention, the target site will generally include a sequence variance site as described above.

Both anti-sense RNA and DNA molecules and ribozymes of the invention may be prepared by any method known in the art for the synthesis of RNA and DNA molecules. See, for example, Draper, supra. hereby incorporated by reference herein. These include techniques for chemically synthesizing oligodeoxyribonucleotides well known in the art such as, for example, solid phase phosphoramidite chemical synthesis. Alternatively, RNA molecules may be generated by in vitro and in vivo transcription of DNA sequences encoding the antisense or ribozyme RNA molecule. Such DNA sequences may be incorporated into a wide variety of vectors which incorporate suitable RNA polymerase promoters such as the T7 or SP6 polymerase promoters. Alternatively, antisense or ribozyme cDNA constructs that synthesize antisense or ribozymes RNA constitutively or inducibly, depending on the promoter used, can be introduced stably into cell lines.

Various modifications to the RNA or DNA molecules may be introduced as a means of increasing intracellular stability and half-life. Possible modifications include but are not limited to the addition of flanking sequences of ribo- or deoxynucleotides to the 5' and/or 3' ends of the molecule or the use of phosphorothioate or methyl phosphonate rather than phosphodiesterase linkages within the oligodeoxyribonucleotide backbone. Modifications may also be made on the nucleotidic sugar or purine or pyrimidine base, such as 2'-O-alkyl (e.g., 2'-O-methyl), 2'-O-allyl, 2'-amino, or 2'-halo (e.g., 2'-F). A variety of other substitutions are also known in the art and may be used in the present invention. More than one type of nucleotide modification may be used in a single modified oligonucleotide.

A specific application of generating inhibitors which are either complementary oligonucleotides or inhibitory oligopeptides is described in Holzmayer, Pestov, and Roninson, "Isolation of dominant negative mutants and inhibitory antisense RNA sequences by expression selection of random DNA fragments," *Nucleic Acids Research* 20:711–717 (1992). In this study, genetic suppressor elements (GSEs) are identified by random DNA fragmentation and cloning in expression plasmids.

Preferred oligonucleotide inhibitors include oligonucleotide analogues which are resistant to degradation or hydrolysis by nucleases. These analogues include neutral, or nonionic, methylphosphonate analogues, which retain the ability to interact strongly with complementary nucleic acids. Miller and Ts'O, *Anti-Cancer Drug Des.* 2:11–128 (1987). Further oligonucleotide analogues include those containing a sulfur atom in place of the 3'-oxygen in the phosphate backbone, and oligonucleotides having one or more nucleotides which have modified bases and/or modified sugars. Particularly useful modifications include phosphorothioate linkages and 2'-modification (e.g., 2'-O-methyl, 2'-F, 2'-amino).

V. Pharmaceutical Formulations and Modes of Administration

The particular compound, antibody, antisense or ribozyme molecule that exhibits allele specific inhibitor activity can be administered to a patient either by itself, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of one or more symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et. al., in *The Pharmacological Basis of Therapeutics*, 1975, Ch. 1 p.1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran.

Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Factors specific for the delivery of antisense and ribozyme nucleic acids are known in the art, for example as discussed in Couture et al., WO 94/02595, which is hereby incorporated herein by reference. This reference also describes the synthesis of nucleic acid molecules having a variety of 2' modified nucleotides.

The references cited herein are incorporated by reference to the same extent as if each had been individually incorporated by reference. The invention is illustrated further by the following examples, which are not to be taken as limiting in any way. The examples, individually, and together, further demonstrate that one skilled in the art would be able to practice each of the steps in developing useful pharmaceutical products as described in the invention. Generally, the development of such a product involves the following steps:

1. Select candidate target gene essential for cell survival or proliferation.
2. Determine chromosome location and LOH frequency.
3. Identify common variance in the normal population.
4. Demonstrate antiproliferative effects from inhibition of candidate gene.
5. Design variance-specific inhibitor.
6. Achieve variance-specific antiproliferative effects in cancer cells.

EXAMPLES

Example 1

Dihydropyrimidine Dehydrogenase (DPD)
DPD is Conditionally Essential

Dihydropyrimidine Dehydrogenase is essential for cell survival in the presence of pyrimidine nucleotide analogs such as 5-FU and fluorodeoxyuridine. 5-fluorouracil (5-FU) and related compounds are antineoplastic drugs used in the treatment of breast, gastrointestinal, head and neck and other cancers. These drugs have widely varying clinical effects in cancer patients, ranging from induction of complete response (tumor disappearance) in some patients to severe toxicity in others. There is currently no reliable basis for predicting individual patient responses, and therefore patients receiving 5-FU must be monitored carefully for toxic reactions.

There are a variety of anabolic and catabolic pathways that affect the action of 5-FU (reviewed in Goodman and Gilman, The Pharmacological Basis of Therapeutics, 8th edition). For example, in order to exert its antiproliferative effects the pyrimidine analog 5-FU must be converted enzymatically to the nucleotide level (fluorodeoxyuridine) by phosphorylation and ribosylation; fluorodeoxyuridine is sometimes given directly because it bypasses most of these steps, and simply requires phosphorylation by thymidine kinase. The 5-fluoronucleotide is an irreversible inhibitor of thymidylate synthase, the enzyme which converts dUMP to dTMP and is required for de novo synthesis of thymidine, and hence for DNA synthesis.

There is a three step pathway for catabolism of pyrimidines (thymine and uracil) to beta alanine. Pyrimidine analogs such as 5-FU are catabolized by the same pathway. The first and rate limiting step in this pathway is catalyzed by dihydropyrimidine dehyrogenase (DPD). DPD accounts for catabolism of as much as 90% of a 5-FU dose in normal individuals, and the half life of 5-FU in normals is ~8–20 minutes. Patients homozygous for mutant DPD alleles have been identified, a condition variously called DPD Deficiency, Hereditary Thymine-Uraciluria or Familial Pyrimidinemia. In such patients ~90% of 5-FU is excreted unchanged in the urine, and the drug has a half life longer that 2.5 hours. As a result of the drastically reduced catabolism of 5-FU the toxic effects of the drug are magnified and patients are subject to severe toxic reactions. There are reports of deaths in patients with DPD deficiency after treatment with 5-FU. Thus cell (and organism) survival in the presence of 5-FU depends on presence of functional DPD protein to transform 5-FU to the inactive dihydroxy metabolite.

This principal has also been demonstrated in cancer cells both in vitro and in vivo: cancer cells with lower DPD levels are more susceptible to the toxic effects of 5-FU. It has been suggested that measuring DPD levels would be useful for calibration of 5-FU dosage.

The DPD Gene Exhibits Variances

We have identified four common sites of variance in DPD mRNA by screening cDNA from 36 unrelated individuals. The variant nucleotides are 166, 577, 3925 and 3937 (see DPD Variance Table; numbering is from Yokota, et al. cDNA Cloning and Chromosome Mapping of Human Dlhydropyrimidine Dehydrogenase, an Enzyme Associated with 5-fluorouracil Toxicity and Congenital Thymine Uraciluria. Journal of Biological Chemistry. 269: 23192–23196, 1994). Two of the variances in nucleotide sequence alter the amino acid coding sequence: amino acid 29 is usually cysteine but arginine alleles were also detected; cys/arg heterozygotes were found at a frequency of 11%. Residue 166 of DPD is reported to be methionine but valine is present at 166 in some alleles; 9% of the population surveyed are met/val heterozygotes. One double heterozygote was identified out of 36 patients. Both these amino acid polymorphisms are located in the N-terminal NAD/FAD binding domain of DPD. Residue 166 is located in a highly conserved domain of DPD. Two other polymorphisms are located in the 3' untranslated region of DPD, only 11 nucleotides apart.

The DPD Gene Maps to Chromosome 1p22, a Region Frequently Subject to LOH in Different Cancers The DPD gene has been mapped to chromosome 1p22 by fluorescense in situ hybridization. LOH at 1p22 has been reported in colon, breast, and other cancers.

Allele Specific Inhibition of DPD to Potentiate 5-FU Action in Cancer Cells with LOH at the DPD Locus The DPD gene is polymorphic and conditionally essential in the presence of 5-FU. These properties can be exploited in a therapeutic strategy for cancer patients with LOH at the DPD locus. Specifically, in a patient with two alternative alleles for DPD in normal cells and one allele in cancer cells due to LOH, an allele specific drug can be used to sensitize cancer cells to the action of 5-FU by inhibiting its catabolism. Cancer cells (but not normal cells) would be poisoned by high levels of 5-FU due to low clearance. Normal cells, containing an uninhibited allele, would be able to catabolize DPD at close to normal levels.

Alternatively, patients heterozygous for functional and defective copies of DPD, and in whom LOH resulted in loss of the functional allele, could be treated by 5-FU without the necessity for an allele specific inhibitor. Identification of such patients would require a test for heterozygosity at DPD and a test for LOH which could show which allele is deleted in cancer cells. Such an approach would be expected to identify patients likely to respond well to 5-FU even though they might have cancers not traditionally treated with pyrimidine analogs.

Example 2

Fanconi Anemia Genes A, B, C, D, E, F, G and H (FAA, FAB, FAC, FAD, FAE, FAF, FAG, FAH)

The Fanconi Anemia Genes are Conditionally Essential.

The Fanconi Anemia genes are essential for cell growth or survival in the presence of DNA cross linking agents. In order for cells to survive or proliferate in an abnormal environment characterized by the presence of DNA cross linking molecules such as Mitomycin C and diepoxybutane it is necessary that the cells are capable of efficiently repairing damage caused by these agents. Cells contain proteins necessary for such repair. One way such repair proteins can be identified is by absence of function in specific patients who, as a consequence, are particularly susceptible to the toxic effects of cross linking agents.

Fanconi Anemia (FA) is a hereditary disease, autosomal recessive in transmission, characterized by progressive bone marrow failure, birth defects and predisposition to malignancies. FA patients are hypersensitive to the toxicity of DNA cross linking agents. This hypersensitivity can be measured in cultured FA cells, which is one method used to establish the diagnosis of FA.

Patients heterozygous for defective FA genes are generally not hypersensitive to DNA crosslinking agents in contrast to those that are homozygous. This suggests that treating heterozygous cancer patients with an inhibitor specific for one allele of the FA gene (and thereby reducing levels of FA protein finction by up to 50% in normal cells) would be well tolerated. Inhibition of the FA allele present in cancer cells but not the alternative form present only in normal cells would make cancer cells selectively sensitive to crosslinking agents, leading to a cytotoxic antiproliferative effect. Normal cells would be able to repair damage caused by such agents, by analogy to the clinical data from patients heterozygous for defective FA genes.

The FA Genes and Gene Products are Polymorphic

Seven FA genes have been identified by complementation studies. The genes for FAA and FAC have been cloned. DNA variances have been reported in both genes. For example, Savino et al. report three variances in FAA, all of which alter the protein coding sequence. (Savino, M., et al. Mutations in the Fanconi Anemia Group A Gene (FAA) in Italian Patients. American Journal of Human Genetics 61:1246–1253, 1997.) The location of these variances is shown in the Table below, reproduced from the paper by Savino.

Variances in the FAA Gene

| Polymorphic nucleotide | Alternate bases | Affected amino acid residue | Alternate amino acids | Frequency of rare allele |
|---|---|---|---|---|
| 796 | A, G | 266 | Thr, Ala | .29 |
| 1501 | G, A | 501 | Gly, Ser | .40 |
| 2426 | G, A | 809 | Gly, Asp | .30 |

FA Genes Map to Chromosomes that are Frequently Subject to LOH in Different Cancers The FAC gene maps to chromosome 9q22.3, (as do three other FA complementation groups according to Strathdee, C. A., et al. Evidence for at least four Fanconi anaemia genes including FACC on chromosome 9. *Nature Genetics* 1: 196–198, 1992). The FAA gene maps to chromosome 16q24.3. FAD maps to 3p26-p22. All FA genes mapped so far lie in regions subject to frequent LOH. LOH affecting chromosome 9 is well documented in many cancers. For example, loss of the 9q arm is well documented in cancers such as bladder, esophagus, ovary, testis and uterus. LOH frequencies in these cancers range from 20% to 62%. LOH affecting chromosome arm 16q, particularly the 16q24 region is well documented, particularly in breast, prostate and liver cancers. For example, in six detailed studies of breast cancer in the 16q22–q24 region LOH frequencies of 40–60% have been reported. Further, 16q22 LOH has been reported in 25–90% of liver cancers, with the average around 45%. Less extensive studies of other cancer types report 16q22 LOH in 19% of bladder cancers, 20% of colon cancers, 19–27% of esophageal cancers, 25% of small cell lung cancers, 16–37% of ovarian cancers 22% of uterine cancers, and 31–50% of prostate cancers. Loss of chromosome 3p26–21 is common in lung cancer, kidney cancer, head and neck cancer and breast cancer among other cancers. Reports of >50% LOH are common in these cancer types.

Other Genes Conditionally Essential for Response to DNA Cross Linking Agents

In a related aspect, other genes which, when defective, sensitize cells to toxic effects of DNA crosslinking agents would be amenable to the therapeutic strategy outlined above for the FA genes. Specifically, in a patient with two alternative alleles for such a gene and LOH at the relevant locus, an allele specific drug could be used to sensitize cancer cells to the action of cross linking agents. Such drugs could then be used to treat cancer patients constitutionally heterozygous for two normal alleles at the relevant locus, in whom LOH had rendered cancer cells hemizygous or homozygous for one allele. Treatment would consist in the administration of the appropriate allele specific inhibitor plus a cross linking agent or treatment to induce damage in all cells. Cancer cells (but not normal cells) would be rendered unable to respond by inhibition of expression of the relevant repair gene. Examples of such genes are the excision repair cross complementing (ERCC) genes, twelve of which have been identified (see Target Gene Table). Defects in these genes are associated with Xeroderma Pigmentosum and Cockayne Syndrome. (Scriver, C. R. et al., The Metabolic and Molecular Bases of Inherited Disease, 7th edition, McGraw Hill, New York, 1995.)

Alternatively, patients heterozygous for functional and defective copies of such genes, and in whom LOH resulted in loss of the functional allele, could be treated by a cross-link inducing procedure without the necessity for an allele specific inhibitor. Identification of such patients would require a test for heterozygosity at the target locus and a test for LOH which could show which allele is deleted in cancer cells. Such an approach would be expected to identify patients likely to respond well to cross linking agents or procedures even though they might have cancers not traditionally treated with such agents.

Example 3

Asparagine Synthetase (AS)

Variagenics Target Gene

Asparagine Synthase is Conditionally Essential

Cells require a continuous supply of amino acids for protein biosynthesis. Cells can import amino acids from serum via amino acid transporters (the only source besides protein catabolism for the ten essential amino acids), or amino acids cells can be synthesized de novo by cells (only an option for the ten nonessential amino acids). The essential amino acids are isoleucine, leucine, lysine, methionine, phenylalanine, threonine, tryptophan, valine and histidine. Alterations in the nutritional environment of growing cells that result in a decreased extracellular concentration of essential amino acids cause arrested cell growth and may result in cell death.

Even a nonessential amino acid can become essential in a cell where (i) at least one enzyme required for its biosynthesis is not expressed (perhaps due to downregulation in response to an abundant extracellular supply of the amino acid), or (ii) the biosythetic pathway is blocked by an inhibitor.

Asparagine is a nonessential amino acid which is, however, essential for survival of rapidly dividing cells that are not expressing asparagine synthetase, the terminal enzyme in asparagine biosynthesis. Asparagine synthetase, considered to be a housekeeping gene, catalyzes the ATP dependent conversion of aspartic acid to asparagine in mammalian cells. A number of different cancer types do not usually express asparagine synthetase, including childhood acute leukemias. One common therapeutic used in the treatment of childhood acute lymphocytic leukemia is the enzyme L-asparaginase (purified from *E. coli* or *Erwinia carotovora*) which, upon injection, rapidly depletes serum asparagine (by hydrolysis to aspartate), thereby lowering blood levels of asparagine to undetectable levels within hours of injection. (Ohnuma, T. et al. Biochemical and Pharmacological Studies with L-Asparaginase in Man. Cancer Research 30: 2297–2305, 1970.) Leukemic cells have high rates of protein synthesis but do not express asparagine synthetase and are therefore highly vulnerable to the rapid loss of asparagine and consequent shutdown of protein synthesis. Cell death after L-asparaginase induced asparagine starvation has been shown to be apoptotic. (Bussolati, O. Characterization of Apoptotic Phenomena Induced by Treatment with L-Asparaginase in NH3T3 Cells. Experimental Cell Research 220: 283–291, 1995.) After one or more doses leukemic cells often become resistant to L-asparaginase due to induction of asparagine synthetase activity and consequent autonomy for asparagine.

In a patient with two alternative alleles for asparagine synthetase and LOH at 7q, an allele specific drug could be used to sensitize cancer cells to the action of L-asparaginase. Such drugs could then be used to treat cancer patients constitutionally heterozygous for two normal alleles at the asparagine synthetase locus, in whom LOH had rendered cancer cells hemizygous or homozygous for one allele. Treatment would consist in the administration of the appropriate allele specific inhibitor plus L-asparaginase to deplete the concentration of this amino acid in serum while rendering cancer cells (but not normal cells) unable to respond by upregulating asparagine synthetase.

The Asparagine Synthetase Gene Maps to Chromosome 7q21.3, a Region Frequently Subject to LOH in Different Cancers The asparagine synthetase gene has been mapped to chromosome 7q21.3 by fluorescence in situ hybridization, following localization to 7q by analysis of somatic cell hybrids. The q21 region of chromosome 7 is subject to frequent LOH, particularly in colon, breast and prostate cancers. 7q21.3 LOH is detected in up to 50% of colon cancers, up to 37% of prostate cancers (83% of prostate cancers have LOH in the adjacent chromosome band, 7q31) and in 10–55% of breast cancers, where again, there is even more frequent LOH in 7q31. LOH at 7q21 has also been reported in uterine cancer and head and neck cancer. Several other cancer types have not yet been well studied for LOH affecting this region.

Example 4

Methionine Synthase (MS)

Variagenics Target Gene

Methionine Synthase is Conditionally Essential in Dividing Cells

Cells require a continuous supply of amino acids for protein biosynthesis. L-methionine is one of ten essential amino acids. Consequently dividing cells must obtain their methionine from serum via amino acid transporter (the only source besides protein catabolism for the ten essential amino acids). Alterations in the nutritional environment of growing cells that result in a decreased extracellular concentration of essential amino acids such as methionine cause arrested cell growth and may result in cell death. Cancer cells are particularly sensitive to methionine deprivation. (Tan, Y., et al., Anticancer Efficacy of Methioninase in vivo. *Anticancer Research* 16: 3931–3936.)

The cellular requirement for methionine can be bypassed: if L-homocysteine is provided to cells it can be methylated to form methionine by the enzyme methionine synthase (MS). In this reaction the methyl group is provided by 5-methyltetrahydrofolate and MS-bound methylcobalamin serves as an intermediate methyl carrier. A second enzyme may be required for reductive activation of methionine synthase, based on complementation studies.

It was realized that the apparent antineoplastic effects of methionine deprivation could be enhanced and made tumor cell specific by preventing cells from converting endogenous homocysteine to methionine by allele specific inhibition of methionine synthase (or other enzymes required for the conversion of homocysteine to methionine; see: Scriver, C., et al., editors, *The Metabolic and Molecular Basis of Inherited Disease*. McGraw Hill, New York, pp. 3111–3128 and 3129–3149). This strategy would be useful in cancer patients that are heterozygous for methionine synthase (or another enzyme required for conversion of homocysteine to methionine) and who have LOH at the methionine synthase (or other) gene locus. In such patients an allele specific inhibitor of MS directed to the sole allele present in cancer cells, coupled with methionine starvation or methioninase treatment, would selectively prevent tumor cells from responding to methionine deprivation. The provision of supplemental homocysteine, which could only be converted to methionine by the normal cells, would provide a way to amplify the differential toxicity to cancer cells. Also, the methionine analog ethionine has been shown to potentiate the effects of methionine starvation. (Poirson-Bichat, F., et al., Growth of methionine-dependent human prostate cancer (PC-3) is inhibited by ethionine combined with methionine starvation. Br. J. Cancer 75: 1605–1612.) Ethionine or similar agents could be used in conjunction with an allele specific inhibitor of methionine synthesis.

An alternative approach to allele specific therapy of cancer cells with LOH would be to target the amino acid transport system for methionine in patients heterozygous for this protein and in whom only one allele is present in cancer tissue as a result of LOH. This would result in selective methionine starvation for cancer cells. Allele specific transport inhibition could be combined with methionine starvation or methioninase treatment to enhance the cytotoxic effect.

The Methionine Synthase Gene Maps to Chromosome 1q43, a Region Subject to LOH in Several Cancers The MS gene has been mapped to chromosome 1q43 by fluoresence in situ hybridization. The q43 region of chromosome 1 is subject to frequent LOH particularly in colon, head and neck, ovarian and liver cancers, where LOH frequencies vary from 11 to 39%. LOH at 1q43 has also been reported in cervix, pancreas, stomach and testis cancers. Several other cancer types have not yet been well studied for LOH in this region.

Other Amino Acid Biosynthetic Enzymes are Candidates for Allele Specific Inhibition It will be evident to one skilled in the art that strategies similar to those described above for asparagine (an essential amino acid) and methionine (a non-essential amino acid) could be undertaken for other amino acid biosynthetic enzymes. For example, L-glutaminase has also been shown to have antiproliferative effects on mammalian cell growth. Allele specific blockade of glutamine synthesis in heterozygous patients with LOH for genes essential for glutamine synthesis could be the basis of a cancer specific therapy.

Example 5

Methylthioadenosine phosphorylase (MTAP)
Variagenics Target Gene
Methylthioadenosine Phosphorylase can Convert Methylthioadenosine to Methionine, an Essential Amino Acid Cells require a continuous supply of amino acids for protein biosynthesis. L-methionine is one of ten essential amino acids. Consequently dividing cells must obtain methionine from serum via amino acid transporter (the only source besides protein catabolism or conversion of L-homocysteine). Alterations in the nutritional environment of growing cells that result in a decreased extracellular concentration of essential amino acids such as methionine cause arrested cell growth and may result in cell death. Cancer cells are particularly sensitive to methionine deprivation. (Tan, Y., et al., Anticancer Efficacy of Methioninase in vivo. *Anticancer Research* 16: 3931–3936.)

The cellular requirement for methionine can be bypassed by conversion of L-homocysteine to methionine as discussed above. An alternative pathway for methionine synthesis is conversion of 5'-methylthioadenosine (5'-MTA) via the action of 5'-MTA phosphorylase (MTAP). (Tisdale, M. J., Methionine Synthesis from 5'-methylthioadenosine by Tumor Cells. *Biochemical Pharmacology* 32: 2915–2920.) In tissue culture experiments low concentrations of 5'-MTA can substitute for methionine in some cell lines. Thus 5'-MTA can rescue cells from methionine deprivation.

It occured to the inventors that allele specific inhibition of MTAP in cancer patients heterozygous for MTAP and whose cancer cells have only one allele of MTAP as a consequence of LOH, in combination with methionine deprivation (methionine starvation or L-methioninase treatment) and dietary supplementation with 5'-methylthioadenosine would provide a source of convertible methionine substrate selectively useful to normal cells. Tumor cells would have no source of methionine, being unable to convert the 5'-methylthioadenosine, and hence would be selectively poisoned. This therapeutic strategy would not necessarily require an allele specific inhibitor as all copies of MTAP are deleted in some cancers. Such cancers should be differentially poisoned vis a vis normal cells by methionine deprivation in the presence of 5'-methylthioadenosine.

The MTAP Gene Maps to 9p21, a Region Frequently Subject to LOH in Many Cancers

The MTAP gene has been mapped to chromosome 9p21 by physical techniques (pulsed field gel electrophoresis and yeast artificial chromosome mapping). The gene lies near the cyclin dependent kinase inhibitors p16 and p15 which are frequently reduced to one or zero copies in cancer cells. (Nobori, et al., Genomic cloning of methylthioadenosine phosphorylase: a purine metabolic enzyme deficient in multiple different cancers. *Proc. Natl. Acad Sci. USA.* 93: 6203–6208.) The p21 region of chromosome 9 is subject to frequent LOH particularly in cancers of the bladder, breast, esophagus, head and neck, kidney, lung, melanoma and ovary. The frequency of LOH in these cancers ranges from 20% to nearly 100%.

Example 6

DNA Dependent Protein Kinase (DNA-PK) and Associated Factors
Variagenics Target Genes
DNA Dependent Protein Kinase is Conditionally Essential Cells exposed to ionizing radiation, such as gamma radiation, are damaged by base modifications and DNA strand breaks. Double strand DNA breaks are among the most lethal form of radiation damage; one such break, if unrepaired, can be cell lethal. Four complementation groups of mammalian cell mutants that are defective in repair of double strand (ds) break have been identified. All four complementation groups are hypersensitive to ionizing radiation. The loci for three of these groups have been shown to encode components of DNA-dependent protein kinase (DNA-PK). The fourth group is deficient in the gene encoding XRCC4, a factor that associates with and stimulates DNA Ligase IV. Ligation of ds breaks by DNA ligase IV in a cell free system in increased 7–8 fold by co-expression of XRCC4.

DNA-PK is a multiprotein complex with a DNA binding regulatory subunit, the Ku heterodimer [Ku70 (XRCC6) and Ku80, also referred to as Ku86 (XRCC5)], and a catalytic subunit, DNA-PKcs (probably XRCC7), that is activated by the regulatory subunit upon binding to DNA ds ends, with consequent expression of serine/threonine kinase activity resulting in phosphorylation of a variety of DNA binding proteins. A fourth protein called KARP-1 is expressed from the Ku80/86 locus and is also implicated in DNA-PK function.

Cells lacking any of the components of DNA-PK are exquisitely sensitive to gamma irradation. This has been demonstrated directly in mice with targeted disruption of the Ku80/86 and DNA-PKcs genes. The Ku80/86 deficient mice were also sensitive to methyl methane sulfonate, a DNA alkylating agent that induces single strand breaks and to etoposide, a topoisomerase II inhibitor. Thus the components of DNA-PK can also be important for repair of a variety of chemically induced DNA lesions as well as ionizing radation.

In a cancer patient with two alternative alleles for a component of DNA-PK and LOH at the heterozygous locus, an allele specific inhibitory drug could be used to sensitize cancer cells to the action of ds break inducing treatments. Sucb a drug could be used to treat cancer patients constitutionally heterozygous for two normal alleles at any of the DNA-PK loci in whom LOH had rendered cancer cells hemizygous or homozygous for one allele. Treatment would consist in the administration of the appropriate allele specific inhibitor plus a ds break inducing agent or procedure. The tumor cells would be unable to effectively repair ds breaks, while the uninhibited allele in normal cells would be able to function. Alternatively, patients heterozygous for functional and defective copies of genes required for repair of strand breaks, and in whom LOH resulted in loss of the functional allele, could be treated by a strand break inducing procedure without the necessity for an allele specific inhibitor. Identification of such patients would require a test for heterozygosity at the target locus and a test for LOH which could show which allele is deleted in cancer cells. Such an approach would be expected to identify patients likely to respond well to strand breaking agents or procedures (exposure to ionizing radiation) even though they might have cancers not traditionally treated with such measures.

The Genes Encoding Constituents of DNA-PK Map to Chromosomes Frequently Subject to LOH in Different Cancers The DNA-PKcs gene has been mapped to 8q11, the Ku80/86 gene to 2q11–q13 and the Ku70 gene to 22q11–q13. All three regions are subject to LOH in different cancers. LOH on 2q has been reported in lung ovary and cervical cancers at frequencies ranging from 11% to 39%. LOH for 8q has been reported in cervix, head and neck, kidney, lung, ovary, prostate and testis cancers at frequencies ranging from 20% to 50% of cancers. LOH on 22q has been reported in brain, breast colon, head and neck, lung, ovary, pediatric and stomach cancers at frequencies ranging from 10 to 76%. Several other cancer types have not yet been well studied for LOH affecting either region.

Other Proteins Required for Repair of DNA Strand Breaks are Also Candidates for Allele Specific Therapy of Cancer It will be evident to one skilled in the art that strategies similar to those described above for DNA-PK could be undertaken for other proteins required for repair of DNA strand breaks. For a recent review of such proteins see: Zdzienicka, M. Z., Mammalian mutants defective in the response to ionizing radiation-induced DNA damage. *Mutation Research* 336: 203–213, 1995; Thompson, L. H. and P. A. Jeggo, Nomenclature of human genes involved in ionizing radiation sensitivity. *Mutation Research* 337: 131–134, 1995; Thacker, J. and R. E. Wilkinson, The gentic basis of cellular recovery from radiation damage: response of the radiosensitive irs lines to low-dose rate irradiation. *Radiation Research* 144:294–300,1995. Two other syndromes with hypersensitivity to X-rays are Diamond-Blackfan anemia and aplastic anemia (Diemen, P. C., X-ray-sensitivity of lymphocytes of aplastic- and Diamond-Blackfan-anemia patients as detected by conventional cytogentic and chromosome painting techniques. *Mutation Resarch* 373: 225–235, 1997). Recently evidence of several other genes responsible for DNA double strand break repair has been described. (Nicolas, N., Finnie, N. J., et al., Eur. J. Immunol. 26:1118–1122, 1996.) The above genes which, when defective, sensitize cells to toxic effects of DNA strand breaking agents would be amenable to the therapeutic strategy outlined above for the DNA-PK genes. Specifically, in a patient with two alternative alleles for such a gene and LOH at the relevant locus, an allele specific drug could be used to sensitize cancer cells to the action of strand breaking agents. Such drugs could then be used to treat cancer patients constitutionally heterozygous for two normal alleles at the relevant locus, in whom LOH had rendered cancer cells hemizygous or homozygous for one allele. Treatment would consist in the administration of the appropriate allele specific inhibitor plus a strand breaking agent or treatment to induce damage in all cells. Cancer cells (but not normal cells) would be rendered unable to respond by inhibition of expression of the relevant repair gene.

Alternatively, patients heterozygous for functional and defective copies of genes required for repair of strand breaks, and in whom LOH resulted in loss of the functional allele, could be treated by a strand break inducing procedure without the necessity for an allele specific inhibitor. Identification of such patients would require a test for heterozygosity at the target locus and a test for LOH which could show which allele is deleted in cancer cells. Such an approach would be expected to identify patients likely to respond well to strand breaking agents or procedures (exposure to ionizing radiation) even though they might have cancers not traditionally treated with such measures.

Example 7

Ataxia Telangiectasia Mutated (ATM) and c-Abl Variagenics Target Gene

The Ataxia Telangiectasia Gene is Essential for Cell Growth or Survival in the Presence of Ionizing Radiation or DNA Damaging Molecules In order for cells to survive or proliferate in the presence of ionizing radiation (IR) or radiomimetic chemicals it is necessary that they are capable of efficiently repairing IR induced damage. Cells contain proteins necessary for such repair. One way such proteins can be identified is by their absence in specific patients who are particularly susceptible to the toxic effects of IR.

Ataxia Telangiectasia (AT) is a genetically transmitted autosomal recessive disorder characterized by variable degrees of immunodeficiency, telagiectasia (small blood vessels growing near the surface of the skin or eye), cerebellar ataxia (loss of balance due to abnormal development of the cerebellum) and increased sensitivity to both ionizing radiation and radiomimetic drugs, including bleomycin; AT cells are killed by lower doses of ionizing radiation or radiomimetic drugs than normal cells. Further, heterozygotes for mutant and normal AT alleles have radiation sensitivity close to that of homozygous normals. Therefore cancer cells from individuals heterozygous for null alleles of the AT gene (called ATM) should be highly susceptible to radiation therapy when only the deficient AT allele remains in cancer cells due to LOH, compared to normal cells from the same patients. Such patients could be treated by a DNA damage inducing procedure without the necessity for an allele specific inhibitor. Identification of such patients would require a test for heterozygosity at the target locus and a test for LOH which could show which allele is deleted in cancer cells. Such an approach would be expected to identify patients likely to respond well to strand breaking agents or procedures (such as exposure to ionizing radiation) even though they might have cancers not traditionally treated with such measures. In a related aspect, this approach is applicable to heterozygotes for other genes associated with ATM-mediated radiosensitivity. One such protein is the c-Abl protein tyrosine kinase, which binds to the ATM protein and regulates its function. c-Abl is known to be important in the stress response to ionizing radiation. One of its functions is activation of stress activated protein kinases (SAPKs) after irradiation or exposure to alkylating agents such as cis-platinum or mitomycin C, a response that is defective in ATM cells. Correction of the SAPK activation defect in ATM cells by non-mutant ATM cDNA suggests that the ATM-c-Abl interaction is necesary for the DNA damage response. (Kharbanda, S., et al. *Nature* 376: 785–788, 1995.)

In a cancer patient with two alternative functional alleles for a component of ATM and LOH at the ATM locus, an allele specific inhibitory drug could be used to sensitize cancer cells to the action of DNA damage inducing treatments such as ionizing radiation or radiomimetic drugs. Such an allele specific drug could be used to treat cancer patients constitutionally heterozygous for two normal ATM alleles in whom LOH had rendered cancer cells hemizygous or homozygous for one allele. Treatment would consist of the administration of the appropriate allele specific inhibitor plus a DNA damage inducing treatment or procedure. The tumor cells would be unable to effectively the DNA damage, while the uninhibited allele in normal cells would be able to function. A similar approach could be taken to The ATM Gene is Polymorphic The ATM cDNA is 9.58 kb. Several likely polymorphisms have been identified, although population studies have not yet been performed to determine allele frequencies. One of the reported polymorphisms, an ATG to ATA change in codon 847, results in a methionine vs. isoleucine difference. Thus ATM is potentially targetable at the DNA, RNA and protein levels. It is likely that additional variances will be identified with broader population surveys and computational variance detection.

The ATM Gene Maps to Chromosome 11q23 and the c-Abl Gene Maps to 9q34.1, Two Regions of High Frequency LOH in Different Cancer Types Chromosome 9q34 is lost in a high fraction of bladder, esophagus, ovary, head & neck and testis cancers (17–76%) and in a lesser fraction of breast, liver and prostate cancers and leukemias. Chromosome 11q23 is lost in brain, cervix, esophagus, breast, kidney, colon, stomach, head & neck and lung cancers at frequencies ranging from 16% to 100%.

Other Proteins Required for Repair of DNA Damage are also Candidates for Allele Specific Therapy of Cancer It will be evident to one skilled in the art that strategies similar to those described above for ATM and c-Abl could be undertaken for other proteins required for the stress response to DNA damaging agents, such as other stress activated protein kinases or downstream effector proteins.

Example 39

Small Molecule Inhibitors of Variant Sequences Methylguanine Methyltransferase (MGMT) Gene VARIA 1534

The Methylguanine Methyltransferase Gene is Essential for Cell Growth or Survival in the Presence of Alkylating Agents Methylguanine methyltransferase (MGM) is a nuclear protein that repairs alkylating agent damage, specifically alkylation of the O6 position of guanine bases in genomic DNA. MGMT acts as a suicide protein in removing methyl or alkyl groups from guanine and covalently binding them to cysteine 145 of MGMT. The protein is subsequently degraded; it does not act as an enzyme. O6-benzylguanine is an inhibitor of MGMT that mimics the natural substrate, alkylated DNA; transfer of the benzyl group to cysteine 145 of MGMT inactivates the protein. Concurrent administration of O6-benzylguanine and an alkylating agent such as carmustine (BCNU) or lomustine (CCNU) renders tumor cells more sensitive to the toxic effects of the nitrosoureas by inactivataing MGMT and thereby inhibiting the tumor cells ability to repair alkylated DNA. MGMT is thus a conditionally essential gene in the presence of nitrosoureas and other alkylating agents. The conditional essentiality of MGMT has been demonstrated in mice. Animals homozygous for disrupted MGMT genes are more than ten times as sensitive to alkylating agents as normal mice. The relative sensitivity has been measured as the LD50, the dose required to kill 50% of treated animals. (Tsuzuki, T., et al. Targeted disruption of the DNA repair methyltransferase gene renders mice hypersensitive to alkylating agent. *Carcinogenesis* 17: 1215–1220, 1996.) O6-benzylguanine is being developed as a chemosensitizing agent (with alkylating agents) for treatment of human cancer. This treatment regimen is not specific for cancer cells.

In a cancer patient with two alternative functional MGMT alleles in normal tissues and LOH at 10q23 resulting in only one copy of MGMT in cancer cells, an allele specific inhibitor of MGMT could be used to specifically sensitize cancer cells to the action of alkylating agents. Treatment would consist of the administration of the appropriate allele specific inhibitor (directed to the one allele remaining in cancer cells) plus an alkylating agent. The tumor cells would be unable to effectively repair the alkylating agent induced DNA damage, while the uninhibited allele in normal cells would be able to function. Thus normal cells, including sensitive normal cell populations such as bone marrow stem cells, would be able to tolerate higher doses of alkylating agents than cancer cells.

The MGMT Gene and Encoded Protein are Polymorphic

Four variances in human MGMT have been discovered by the inventors or reported in the literature, including three variances that affect the protein sequence. There is a C/T variance at nucleotide 255 (11% heterozygotes among 36 individuals surveyed) which does not affect the encoded protein. There is a second C/T variance at nt. 346 which results in a L84F amino acid variance (5% heterozygotes among 36 individuals surveyed). There is an A/G variance at nt. 523 which results in a I143V amino acid variance (24% heterozygotes among 36 individuals surveyed). This variance occurs only two residues from the active site cysteine at 145. A fourth variance, G/A has been reported in the Japanese population at codon 160, GGA vs. AGA, resulting in a glycine vs. arginine amino acid variance. Fifteen percent of 40 Japanese individuals studied were heterozygotes for this variance. (Imai, Y., et al. A polymorphism at codon 160 of human O6-methylguanine-DNA methyltransferase gene in young patients with adult type cancers and functional assay. *Carcinogenesis* [London] 16:2441–24445, 1995.)

Allele Specific Inhibitors of MGMT

Two of the amino acid variances in MGMT, at residues 143 and 160, are near the active site of the protein. Substantial work has already been done to characterize the functional consequences of the residue 160 glycine/arginine variance. Studies of MGMT kinetics and activity have shown that the 160arginine allele is at least 20 fold more resistant to O6 benzylguanine inactivation, measured as an increase in the ED50 and or as a reduction in the production of guanine from O6-benzyl[8-3H]guanine. The 160gly and 160arg forms of MGMT were nearly equal in alkyltransferase activity in an assay that measured repair of O6-methylguanine in methylated DNA. These results demonstrate variance-specific effects of a small molecule, O6-benzylguanine, on normal (non-mutant) alleles of the conditionally essential MGMT gene. (Edara, S., et al. Resistance of the human O6-alkylguanine-DNA alkyltransferase containing arginine at codon 160 to inactivation by O6-benzylguanine. *Cancer Research* 56: 5571–5575, 1996)

Administration of O6-benzylguanine to patients who are heterozygous for the variance in their normal cells, and contain only the alternative form of the gene with a glycine residue at position 160 in their cancer cells, together with methylating or chloroethylating agents, will specifically sensitize cancer cells to the cytotoxic effects of the alkylating agents without increasing toxicity to normal cells which, since they contain the O6-benzylguanine resistant 160 arginine form of the protein, will continue to repair alkylated DNA.

There is no published data concerning the residue 143 variance, however the proximity of this variance to the active site—both in the primary sequence and upon inspection of the three dimensional structure of the bacterial AGT protein, a functional and structural homolog of human MGMT—suggests that allele specific drugs could be discovered for this variance.

The structural difference between 143 isoleucine and 143 valine is a hydrophobic methyl group. It is well known that most small molecule protein inhibitors interact via hydrophobic interactions. Favorable Van der Waals distances between hydrophobic groups of a substrate and a ligand are vital for high affinity interaction. One possible mechanism of allele specific inhibition would be to exploit the greater bulk of the isoleucine by finding a small molecule that fits into the active site pocket of the valine allele but has a very unfavorable Van der Waals interaction the methyl group of the isoleucine. Other schemes based on the different size and geometry of isoleucine and valine could also be effective.

One approach to identification of such inhibitors would be to make small molecule libraries in which various positions of guanine are substituted with moities of appropriate size and structure. Such libraries could then be tested in various screens of MGMT activity. The two alleles (143isoleucine and 143valine, or any of the other allele pairs of MGMT described above) would be assayed in parallel. Identification of molecules with allele specific inhibitory activity could be the basis for synthesis of additional libraries in which the moities that are best correlated with differential activity are further varied. Methods for the iterative design of high affinity or highly discriminating small molecule inhibitors are known in the art.

Libraries of restricted size can be screened for allele specific inhibitors using a combinatorial strategy based on known inhibitors of MGMT such as O6-benzyl-guanine. A library or libraries can be constructed in which substitutions are indroduced at positions C6 and N9 which have previously been found to affect inactivation of MGMT, or at positions C2 and N8 which can be easily substituted. For example a series of 4(6)-(benzyloxy)-2,6(4)-diamino-5-(nitro or nitroso)pyrimidine derivatives and analogs in which 4(6) benzyloxy groups were replaced with (2-, 3-, or 4 fluorobenzyl)oxy or (2-, 3-, or 4-pyridylmethyl)oxy groups have been synthesized and tested for MGMT inhibition. (Terashima I., and K. Kohda. Inhibition of human O6-alkylguanine-DNA alkyltransferase and potentiation of the cytotoxicity of chloroethylnitrosourea by 4(6)-(Benzyloxy)-2,6(4)-diamino-5-(nitro or nitroso)pyrimidine derivatives and analogues. *J Med Chem* 41: 503–508, 1998.) Substitutions at N7 have been found to be detrimental in general (Moschel, R. C. et al & Pegg, A. E., *J. Med. Chem.* 35: 4486–4491, 1992).

Combinatorial libraries can be constructed according to a published procedure (Norman, T. C. et al., A Structure-Based Library Approach to Kinase Inhibitors. *J. Am. Chem. Soc.* 118: 7430–7431, 1996) where guanine based libraries were made by anchoring a chemically modified guanine (at C6, C2, or C8) to solid supports at C2 via a glycinamide linkage or at N9 via a hydroxyethyl linkage. Chemical reactions can be carried out to introduce a library of hydrophobic substituents of different size at positions C6, C2, or C8. Hydrophobic substituents of various bulkiness and orientation can be introduced through derivatives of O6-benzyl and O6-phenyl groups, O6-alkyl groups, N9-alkyl groups, and C2-amino-alkyl groups.

Libraries constructed as above can be screened for MGMT activity in several types of assays. Methods for bacterial expression and purification of human MGMT protein have been described (see Edara, et al., cited above). Both allelic forms of MGMT could be screened for repair of alkylated or methylated DNA by measuring transfer of tritium from a tritium labelled (methylated) DNA substrate in the presence of various concentrations of library compounds for various times. Alternatively, library compounds could be tritiated and MGMT proteins could be screened for the rate at which they interact with (either via association or cleavage of a moiety from the compound). Other assays for MGMT activity are known in the art.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The groups of genes and the particular genes described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, those skilled in the art will readily recognize that the methods and inhibitors can utilize a variety of different target genes within the groups described. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

What we claim is:

1. A method for identifying an inhibitor active on a conditionally essential gene subject to loss of heterozygosity in a cancer, said method comprising:
   (a) determining at least two alleles of a said gene;
   (b) testing a potential allele specific inhibitor to determine whether said potential allele specific inhibitor is active on at least one but less than all of said alleles;
   wherein inhibition of expression of at least one but less than all of said alleles or reduction of the level of activity of a product of at least one but less than all of said alleles in the presence of said potential allele specific inhibitor is indicative that said potential allele specific inhibitor is a said inhibitor.

2. A method for producing an inhibitor active on at least one but less than all alternative alleles of a conditionally essential gene having at least two alternative alleles, comprising:
   (a) identifying a conditionally essential gene that has alternative allelic forms in a noncancerous cell, wherein one of said alternative allelic forms is deleted in a cancer cell:
   (b) screening to identify an inhibitor which inhibits said at least one but less than all of said at least two alternative alleles; and
   (c) synthesizing said inhibitor in an amount sufficient to produce an inhibitory effect when administered to a cancer cell having only an allele of said gene inhibited by said inhibitor.

3. The method of claim 1 or 2, wherein said gene is selected from the group consisting of:
   galactose-1-phosphate uridyltransferase, galactose kinase, UDP galactose-4-epimerase, methionine synthase, asparagine synthase, glutamine synthetase, multidrug resistance gne/Pglycoprotein, multidrug resistance associated proteins 1–5, bleomycin hydrolase, dihydropyrimidine dehydrogenase, β-ureidopropoinase, β-alanine synthetase, cytidine deaminase, thiopurine methyltransferase, CYP1A1, CYP1A2, CYP2A6, CYP2A7, CYP2B6, CYP2B7, CYP2C8, CYP2C9, CYP2C17, CYP2C18, CYP2C19, CYP2D6, CYP2E1, CYP2F1, CYP3A3, CYP3A4, CYP3A5, CYP3A7, CYP4B1, CYP7, CYP11, CYP17, CYP19, CYP21, CYP27, glutathione transferase alpha, glutathione transferase theta, glutathione transferae mu, glutathione transferase pi, methylguanine methyltransferase, 3-alkylguanine alkyltransferase, 3-methyladenine DNA glucosylase, DNA dependent protein kinase, catalytic subunit of DNA-PK, DNA binding subunit of DNA-PK Ku-70 or Ku-80 subunit, KARP-1, Poly(ADP-ribose) polymerase, Fanconi Anemia genes A, B, C, D, E, F, G, and H, ERCC-1, ERCC2/XPD, ERCC3/XPB, ERCC4, ERCC5, ERCC6, XPA, XPC, XPE, HHR23A, HHR23B, uracil glycosylase, 3-methyl adenine DNA glycosylase, NF-kappa B, XRCC4, XRCC5/Ku80, XRCC6, XRCC7, glutathione-X-transferase, I-kappa B alpha, HSP70, HSP27, and 9-oxoguanine DNA glycosylase.

4. The method of claim 1 or 2, wherein said inhibitor inhibits expression of at least one but less than all of said alleles.

5. The method of claim 1 or 2, wherein said inhibitor reduces the level of activity of a product of at least one but less than all of said alleles.

6. The method of claim 1 or 2, wherein said conditionally essential gene is essential in repair or prevention of damage by non-naturally occurring molecules.

7. The method of claim 6, wherein said conditionally essential gene is essential in response to damage by molecules that react with nucleic acids.

8. The method of claim 1 or 2, wherein said conditionally essential gene is essential in response to radiation.

9. The method of claim 1 or 2, wherein said conditionally essential gene is essential in the presence of a drug.

10. The method of claim 1 or 2, wherein said inhibitor is a ribozyme.

11. The method of claim 1 or 2, wherein said inhibitor comprises an antisense oligonucleotide.

12. The method of claim 1 or 2, wherein said inhibitor is an antibody or antibody fragment.

13. The method of claim 1 or 2, wherein said inhibitor is a small molecule.

* * * * *